US008258257B2

(12) United States Patent
Lo et al.

(10) Patent No.: US 8,258,257 B2
(45) Date of Patent: Sep. 4, 2012

(54) CLAUDIN-4 BINDING PEPTIDES, COMPOSITIONS AND METHODS OF USE

(75) Inventors: David D. Lo, Del Mar, CA (US); Jun Ling, Clarks Summit, PA (US); Mary M. Hamer, Norco, CA (US); Thejani Rajapaksa, Fontana, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/989,737

(22) PCT Filed: Apr. 30, 2009

(86) PCT No.: PCT/US2009/042221

§ 371 (c)(1),
(2), (4) Date: Jan. 18, 2011

(87) PCT Pub. No.: WO2009/134962

PCT Pub. Date: Nov. 5, 2009

(65) Prior Publication Data

US 2011/0104263 A1 May 5, 2011

Related U.S. Application Data

(60) Provisional application No. 61/049,011, filed on Apr. 30, 2008.

(51) Int. Cl.
*A61K 9/127* (2006.01)
*C07K 4/00* (2006.01)

(52) U.S. Cl. ........ 530/300; 530/327; 530/326; 424/450; 424/185.1; 514/1.7

(58) Field of Classification Search ........................ None
See application file for complete search history.

(56) References Cited

U.S. PATENT DOCUMENTS

| | | | | |
|---|---|---|---|---|
| 5,695,956 | A * | 12/1997 | McClane et al. | 435/69.1 |
| 2002/0193294 | A1* | 12/2002 | Blaschuk et al. | 514/9 |
| 2004/0214783 | A1* | 10/2004 | Terman | 514/33 |
| 2006/0052295 | A1* | 3/2006 | Terman | 514/12 |
| 2008/0020018 | A1* | 1/2008 | Moodley et al. | 424/433 |
| 2009/0291047 | A1* | 11/2009 | Santin | 424/1.11 |
| 2010/0239586 | A1 | 9/2010 | Lo et al. | |

(Continued)

FOREIGN PATENT DOCUMENTS

WO 2005/041865 * 12/2005

OTHER PUBLICATIONS

Harada, Motoki et al, Biochemcical Pharmacology, vol. 73, Mar. 2007, pp. 206-214, Role of Tyrosine residues in modulation of claudin-4 by the C-terminal fragment of *Clostridium perfringens* enterotoxin.*

(Continued)

*Primary Examiner* — Albert Navarro
*Assistant Examiner* — Ginny Portner
(74) *Attorney, Agent, or Firm* — Joseph R. Baker, Jr.; Gavrilovich, Dodd & Lindsey, LLP

(57) ABSTRACT

The disclosure provides methods and compositions useful for treating claudin-4 associated disorders including cell proliferative disorders. The disclosure also provide claudin-family binding peptides useful in the methods of the disclosure.

22 Claims, 14 Drawing Sheets

U.S. PATENT DOCUMENTS

2011/0165195 A1* 7/2011 Kondoh et al. ............ 424/239.1

OTHER PUBLICATIONS

Czeczulin, Jr et al, Infection and Immunity, 1993, vol. 61(8), pp. 3429-3439, Cloning, Nucleotide sequencing and expression of the *Clostridium perfringens* enterotoxin gene in *Escherichia coli*.*

McClane, Bruce A, Toxicon, vol. 34(11/12), pp. 1335-1343, 1996, An overview of *Clostridium perfringens* enterotoxin.*

Ebihara, C et al, Biochemical Pharmacology, vol. 73, pp. 824-830, 2007, Role of Tyr306 in the C-terminal fragment of *Clostridium perfringens* enterotoxin for modulation of tight junction.*

Sugii, S, Japanese Society of Veterinary Science, Dec. 1994, vol. 56(6), pp. 1047-1050, Analysis of multiple antigenic determinants of *Clostridium perfringens* Enterotoxin as Revealed by Use of Different Synthetic peptides.*

Paddock et al., "Identification, Cloning, and Recombinant Expression of Procalin, a Major Triatomine Allergen," J. Immunol. 2001, pp. 2694-2699, vol. 167.

Ebihara et al., "Preparation of a claudin-targeting molecule using a C-terminal fragment of *Clostridium perfringens* enterotoxin," Journal of Pharmacology and Experimental Therapeutics, Sep. 23, 2005, pp. 255-260, vol. 316, No. 1.

Harada et al., "Role of tyrosine residues in modulation of claudin-4 by the C-terminal fragment of *Clostridium perfringens* enterotoxin," Biochemical Pharmacology, pp. 206-214, vol. 73, Mar. 2007.

Kondoh et al., "A novel strategy for a drug delivery system using a claudin modulator," Pharmaceutical Societ of Japan, Sep. 2006, pp. 1783-1789, vol. 29, No. 9.

Kondoh et al., "A Novel Strategy for the Enhancement of Drug Absorption Using a Claudin Modulator," Molecular Pharmacology, 2005, pp. 749-756, vol. 67.

Kominsky et al., "*Clostridium perfringens* enterotoxin as a novel-targeted therapeutic for brain metastasis," Cancer Research, Sep. 1, 2007, pp. 7977-7982, vol. 67, No. 17.

Ling et al., "Structural constraints for the binding of short peptides to claudin-4 revealed by surface plasmon resonance," Journal of Biological Chemistry, Nov. 7, 2008, pp. 30585-30595, vol. 283, No. 45.

Takahashi et al., "Domain mapping of a claudin-4 modulator, the C-terminal region of C-terminal fragment of *Clostridium perfringens* enterotoxin, by site-directed mutagenesis," Biochemical Pharmacology, Jan. 5, 2008, pp. 1639-1648, vol. 75.

Takahashi et al., "Role of C-terminal regions of the C-terminal fragment of *Clostridium perfringens* enterotoxin in its interaction with claudin-4," Journal of Controlled Release, Aug. 8, 2005, pp. 56-62, vol. 108.

Kim, Ji Yun, International Search Report and Written Opinion, PCT/US2009/042221, Korean Intellectual Property Office, Dec. 29, 2009.

* cited by examiner

Binding of Cldn-4 Ecl2 Mimicking Peptides to Cpe30

A

B

Binding Kinetics of Various Peptides to Cldn-4 Mutant R4

| *Peptides* | *Ka (1/Ms)* | *Kd (1/s)* | *KD (nM)* | *Rmax (RU)* |
|---|---|---|---|---|
| Cpe30 | 1.3e5 | 1.28e-3 | 9.87 | 221 |
| Cpe17 | 2.85e5 | 6.06e-4 | 2.12 | 301 |
| CC4P-13 | 1.59e5 | 7.42e-4 | 4.66 | 207 |
| CC4P-13 (R) | 1.6e5 | 4.7e-5 | 0.3 | 372 |
| CC4P-5 | 3.15e5 | 1.41e-3 | 4.46 | 115 |

| | |
|---|---|
| Cpe17: | NSSYSGNYPYSILFQKF |
| CC4P-13: | APWTEHSYYLSL |
| CC4P-5: | SPWSEPAYTLAP |
| cPE30mt2: | NSSYSGNYYSIL |

Binding Motif:  .......Y/W.....(X)$_{3/4}$....Y.Y/X...

⟵

CLAUDIN-4 BINDING PEPTIDES, COMPOSITIONS AND METHODS OF USE

CROSS REFERENCE TO RELATED APPLICATIONS

This application is a U.S. National Stage Application filed under 35 U.S.C. §371 and claims priority to International Application No. PCT/US2009/042221, filed Apr. 30, 2009, which application claims priority to U.S. Provisional Application No. 61/049,011, filed Apr. 30, 2008, the disclosures of which are incorporated herein by reference.

FIELD OF THE INVENTION

The disclosure relates to peptides that bind claudin family polypeptides, compositions and methods of use thereof.

BACKGROUND

Tight junctions or zona occludens assist in providing a regulated barrier between the intercellular spaces within sheets of epithelial or endothelial cells. Such tight junctions are an important aspect of the normal development of tissues such as the skin and mucosal membranes. These junctions may assist in suppressing the formation and spread of tumors. Inadequate or improperly regulated epithelial or endothelial barrier function contributes to the initiation, maintenance, and exacerbation of inflammation in tissues such as the gut, lungs, and other mucosal linings. Tight junctions separate the apical and basolateral regions of these cells' membranes, allowing the establishment of different physiological environments on the opposite sides of a cell sheet, such as the different physiological environments required for transport of materials across the intestinal epithelium.

SUMMARY

Claudin-4 (CLDN4) is a tight junction transmembrane protein, and is an important protein in establishing the transepithelial electrical resistance in the mucosal epithelium barrier. It also is the receptor for the *Clostridium perfringens* enterotoxin (CPE), and has been found to be highly expressed in a variety of solid tumors. It is a component of mucosal immune surveillance by specialized epithelial M cells. The disclosure demonstrates that CLDN4 is a therapeutic target, whether for intentionally disrupting the epithelial barrier, targeting tumors, or targeted delivery of mucosal vaccines or other payloads. The disclosure provides a plurality of peptides specific for binding to the second extracellular loop 2 (Ecl2) of CLDN4. The peptides of the disclosure show similar affinity for CLDN4 as the CPE protein, but due to their small size are likely to be less immunogenic.

The disclosure provides a substantially purified peptide comprising from about 10-15 amino acids and containing a tyrosine or tryptophan separated by 3-4 amino acids followed by 1 or 2 tyrosines and a leucine. The disclosure provides a claudin family polypeptide binding peptide comprising about 8 to 30 amino acids and comprising the amino acid sequence (Y/W)$(Xaa)_{3\ or\ 4}$ YYXaaL (SEQ ID NO:1) wherein Xaa is any amino acid. The disclosure provides a peptide comprising a sequence of between 10-30 amino acids containing a sequence of (Y/W)$(Xaa)_{3\ or\ 4}$ YYXaaL (SEQ ID NO:1). In one embodiment, the peptide comprises at least one D-amino acid. In one embodiment, the peptide comprises a sequence XaaXaaXaaXaa(Y/W)$(Xaa)_{3\ or\ 4}$ YYXaaL (SEQ ID NO:2). In another embodiment, the peptide comprises a sequence XaaXaa(Y/W)$(Xaa)_{3\ or\ 4}$Y(Y/Xaa)(L/I)XaaXaa (SEQ ID NO:3). In specific embodiment, the peptide is selected from the group consisting of: SLDAGQYVLVMKANSSYSGNYPYSILFQKF (SEQ ID NO:4), NSSYSGNYPYSILFQKF (SEQ ID NO:5), SSYSGNYPYSIL (SEQ ID NO:6), NSSYSGNYYSIL (SEQ ID NO:7), ASNSSYSGNYSIL (SEQ ID NO:8), SPWSEPAYTLAP (SEQ ID NO:9), and APWTEHSYYLSL (SEQ ID NO:10). In one embodiment, the peptide binds to a claudin family polypeptide. In a further embodiment, the peptide binds to a claudin-4.

The disclosure also provides fusion peptides or polypeptide comprising a binding peptide as set forth above linked to a small molecule, nanostructure, peptide or polypeptide of interest. In one embodiment, the polypeptide or peptide of interest is a nanoparticle, a vaccine, a small molecule drug, an antibody, or an antigenic composition.

The disclosure also provides retroinverso peptide of the disclosure.

The disclosure also provides a pharmaceutical composition comprising a peptide of the disclosure in a pharmaceutically acceptable carrier.

The disclosure provides a method of modulating inflammation, asthma, allergy, cell proliferative disorders, metastasis of cancer cells, ion transport disorders such as magnesium transport defects in the kidney, inflammatory bowel disease, *Clostridium perfringens* enterotoxin (CPE) infection, myelin sheath formation disorders such as multiple sclerosis (MS), autoimmune encephalomyelitis, optic neuritis, and progressive multifocal leukoencephalopathy (PML) in a subject, comprising administering a peptide of the disclosure either alone, as a fusion or combination with nanoparticle, vaccine, antigen, peptide, polypeptide, small molecule or the like in a pharmaceutically acceptable carrier. In one embodiment, the allergen is selected from the group consisting of dust mite allergens, pollen, food allergens, drugs like penicillin, and the like.

The disclosure also provides a method of targeting a therapeutic or diagnostic to mucosal M cells comprising linking a therapeutic moiety or diagnostic to a binding peptide of the disclosure to generate a fusion construct and contacting a mucosal M cell with the fusion construct. In one embodiment, the mucosal M cell is in vivo. In another aspect, the therapeutic moiety is a cytotoxic drug, an immunopotentiating drug, an inhibitory nucleic acid molecule, a peptide, a polypeptide or a peptidomimetic.

Also provided by the disclosure is a vaccine comprising a binding peptide of the disclosure linked to an immunogenic molecule. In one embodiment, the vaccine comprises a fusion polypeptide comprising the binding peptide and an immunogenic molecule. In another embodiment, the immunogenic molecule is an HA antigen.

The details of one or more embodiments of the disclosure are set forth in the accompanying drawings and the description below. Other features, objects, and advantages will be apparent from the description and drawings, and from the claims.

Figure 2:
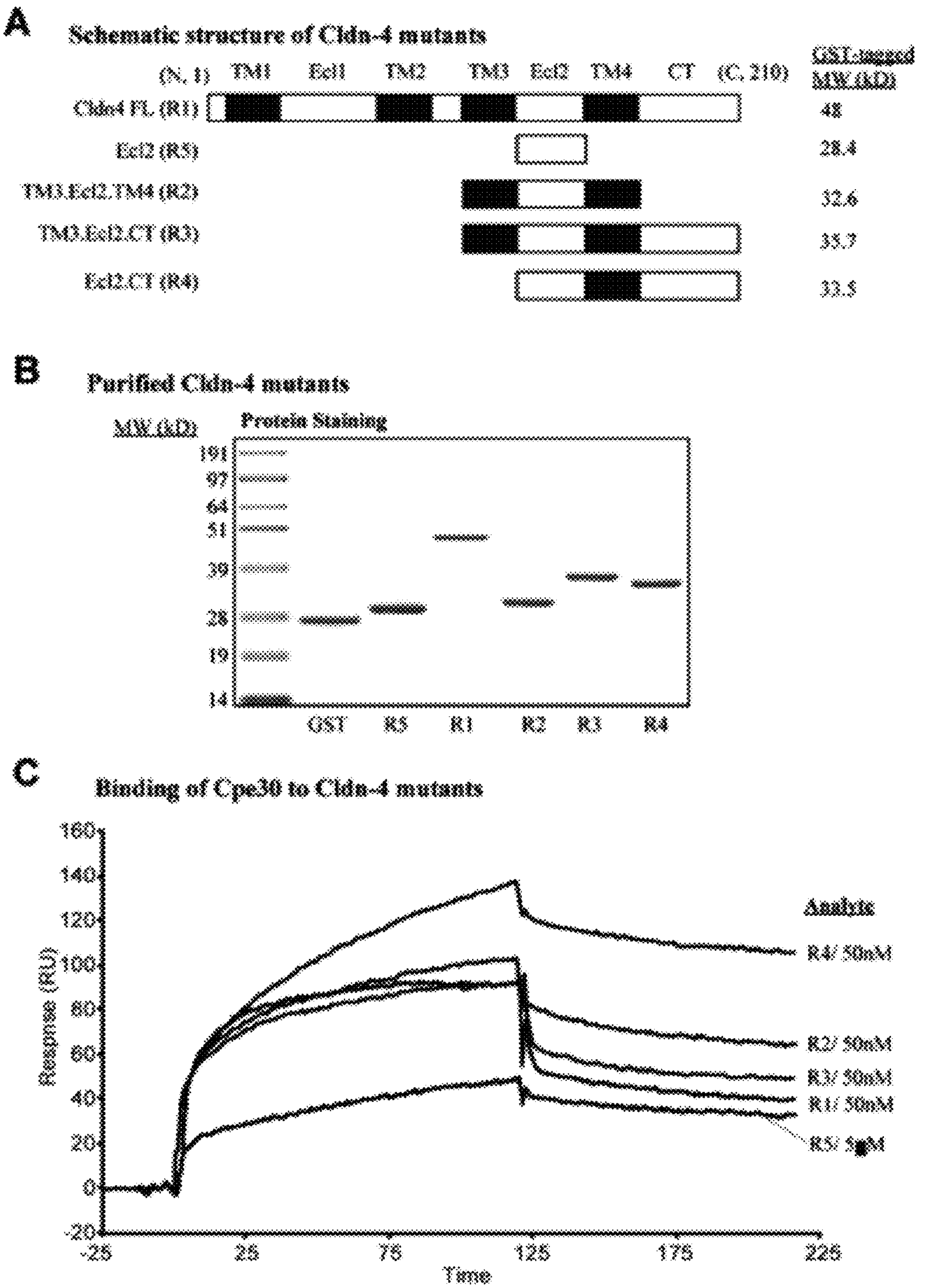

FIG. 2A-C shows Ecl2 with downstream transmembrane domain is sufficient enough to express optimal binding activity to Cpe30. Biotin-Cpe30 was immobilized on an SA chip as the ligand, and a series of Cldn-4 deletion mutant proteins fused to GST were utilized as analytes. (A) The schematic diagram of full-length claudin-4 and its mutants, with the structural domains labeled above. (B) The SDS-PAGE analysis of purified GST-Cldn-4 mutant fusions. (C) Overlay of the sensorgrams from different analytes at medium concentration. GST protein only did not bind Cpe30. Specific binding was identified by subtraction of the control channel from the assay channel; this processing was applied to the rest of experiments in the study.

Figure 3:
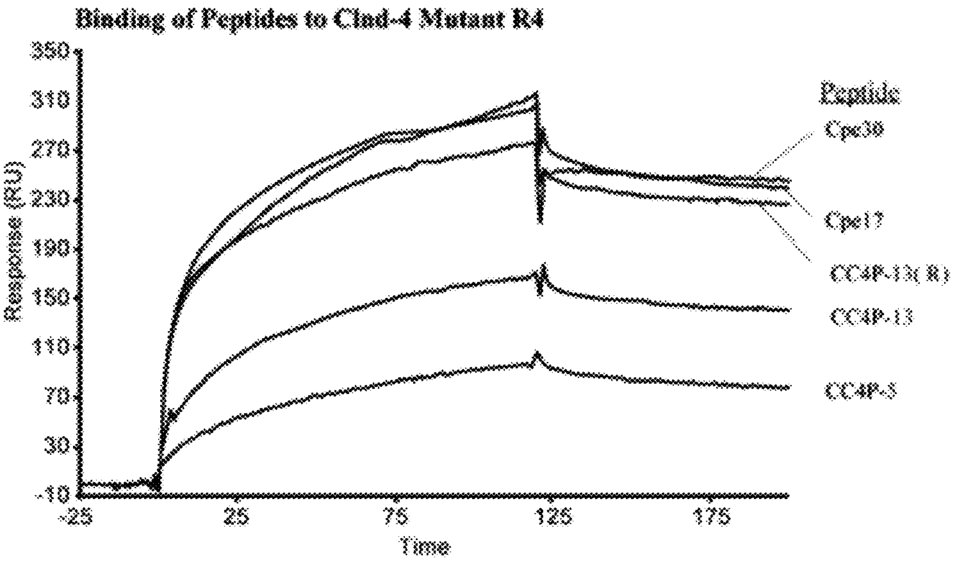

FIG. 3 shows binding kinetics of peptides to GST.Cldn4-Ecl2 mutant R4Biotinylated peptides shown in the figure were immobilized to an SA chip as the ligands, the GST-Cldn4.R4 was used as the analyte from 10 nM to 100 nM to measure the kinetics of binding. The processed specific binding sensorgrams are presented for each ligand. The 50 nM analyte concentration was repeated twice to confirm reproducibility. The binding kinetics was analyzed by "BIAevalution 3.1" software with 1:1 (langmuir) binding mode, and the binding constants were summarized in the table. CC4P-2 peptide had no specific binding to GST.Cldn4-Ecl2, as the assay and control channels responded similarly to the different concentrations of analyte.

Figure 4:
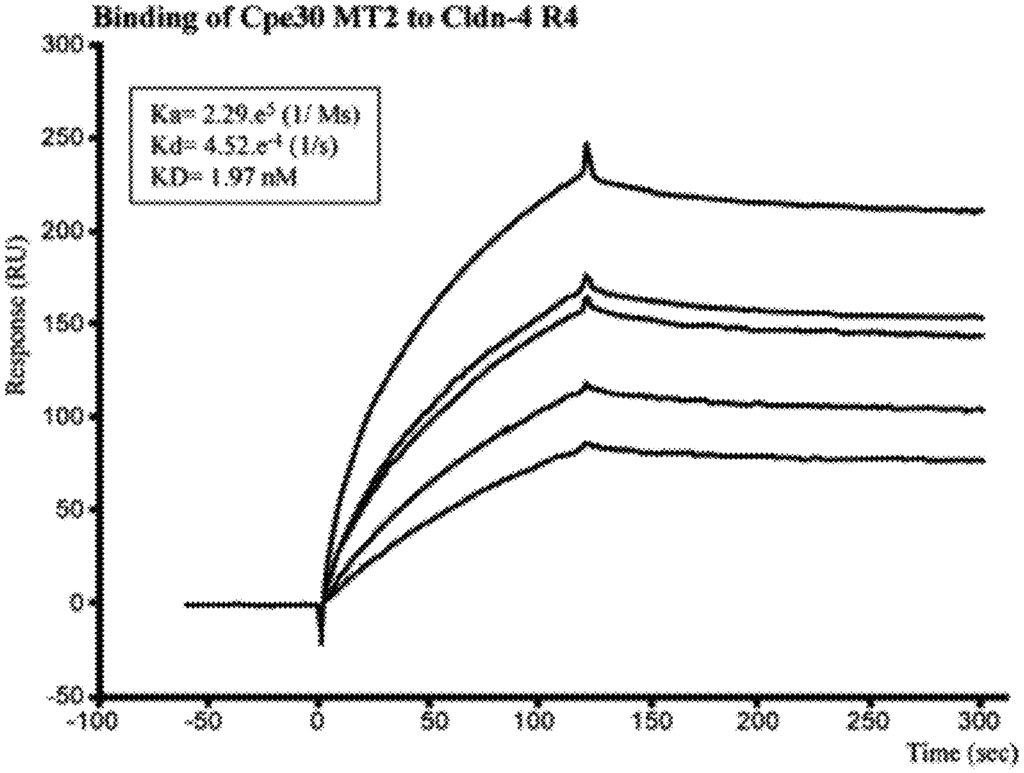

FIG. 4 shows Cpe30 mutant MT2 exhibits specific binding to GST-Cldn4.R4. Cpe30 was reduced to shorter 12 amino acid peptides as indicated in Table 1 (Cpe30MT1 through MT3), and tested against GST-Clnd-4.R4 as described for FIG. 3. Cpe30 MT2 was found to specifically interact with Cldn4 Ecl2; the sensorgrams are shown here. Cpe30 MT1 and MT3 did not bind Cldn4 Ecl2.

Figure 5:
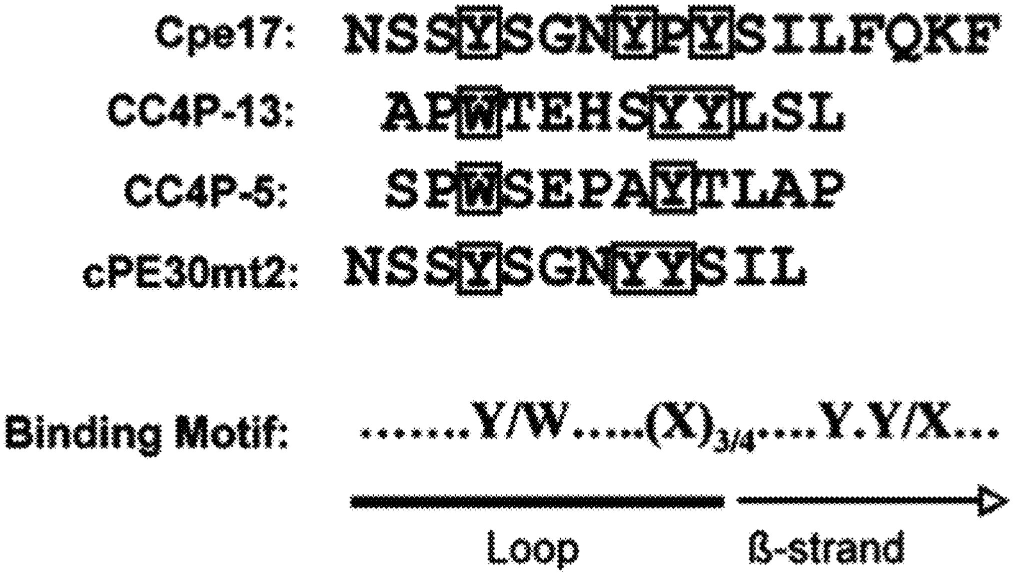

FIG. 5 shows claudin-4 Ecl2 binding motif of peptide ligands. The Cpe17 (SEQ ID NO:5) sequence was aligned with several Ecl2-binding peptides found to have significant affinity (CC4P-13: SEQ ID NO:10; CC4P-5: SEQ ID NO: 9; cPE30mt2: SEQ ID NO: 7; and Binding Motif: SEQ ID NO: 2). The structure-based alignment was performed according to the crystal structure of C-terminus of Cpe. A common binding motif was deduced, with the underlined tyrosine or tryptophan constituting a structural requirement for docking of peptide into the Ecl2 cleft.

FIG. 6A-B shows Cpe30 in recombinant influenza hemagglutinin (HA) retains binding activity to Cldn-4 Ecl2. C-terminally His tagged HA-ts-Cpe30 and HA (shown in (A) were expressed in Baculovirus and purified to homogeneity. HA-specific antibody (H36) was immobilized to a CM5 chip by amine coupling, which was used to capture HA-ts-Cpe30 or HA protein as the ligand. Cldn-4 Ecl2.R4 was used as the analyte. (B) The overlay of sensorgrams of HA-is-Cpe30 with different concentrations of Cldn-4.R4 show the specific interaction. HA protein without Cpe30 showed no binding to Cldn-4 Ecl2; the figure shows that the assay and control channels responded similarly at different concentrations of analyte.

Figure 7:
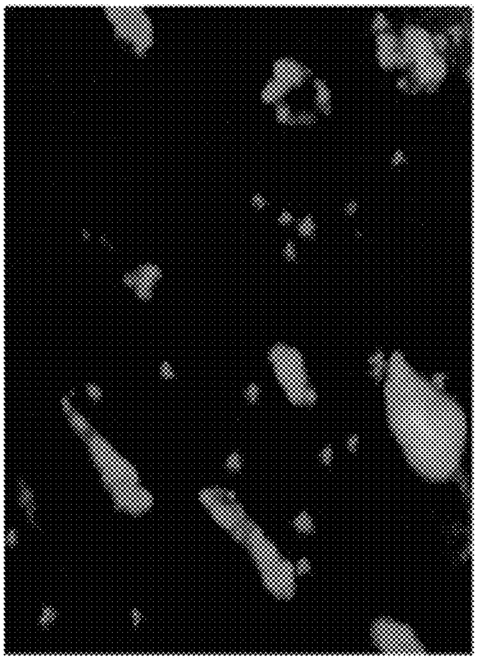

FIG. 7 shows bead uptake by M cells using claudin 4-targeting peptide. A suspension of $10^9$ fluorescent microbeads (0.2 micron) coated with targeting peptide Cpe30 were instilled into nasal passages, and 10 minutes later the NALT was dissected for bead counting. Shown are UEA-1+ M cells (green) in whole mount NALT; BALB/c take up Cpe30-coated beads (red) in large numbers.

Figure 8:
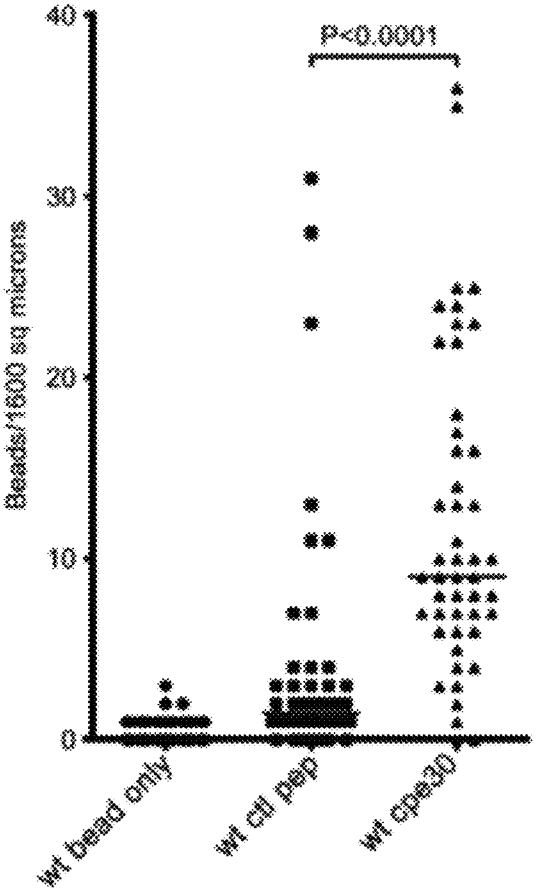

FIG. 8 shows analysis of bead uptake by M cells in NALT. Counts are shown as beads per 1600 sq. micron area (40×40 micron), from multiple measurements from confocal images from at least three mice per group. Low uptake was seen for beads with no peptide and beads with control peptide. High uptake was measured for beads coated with Cpe30 peptide.

Figure 9:
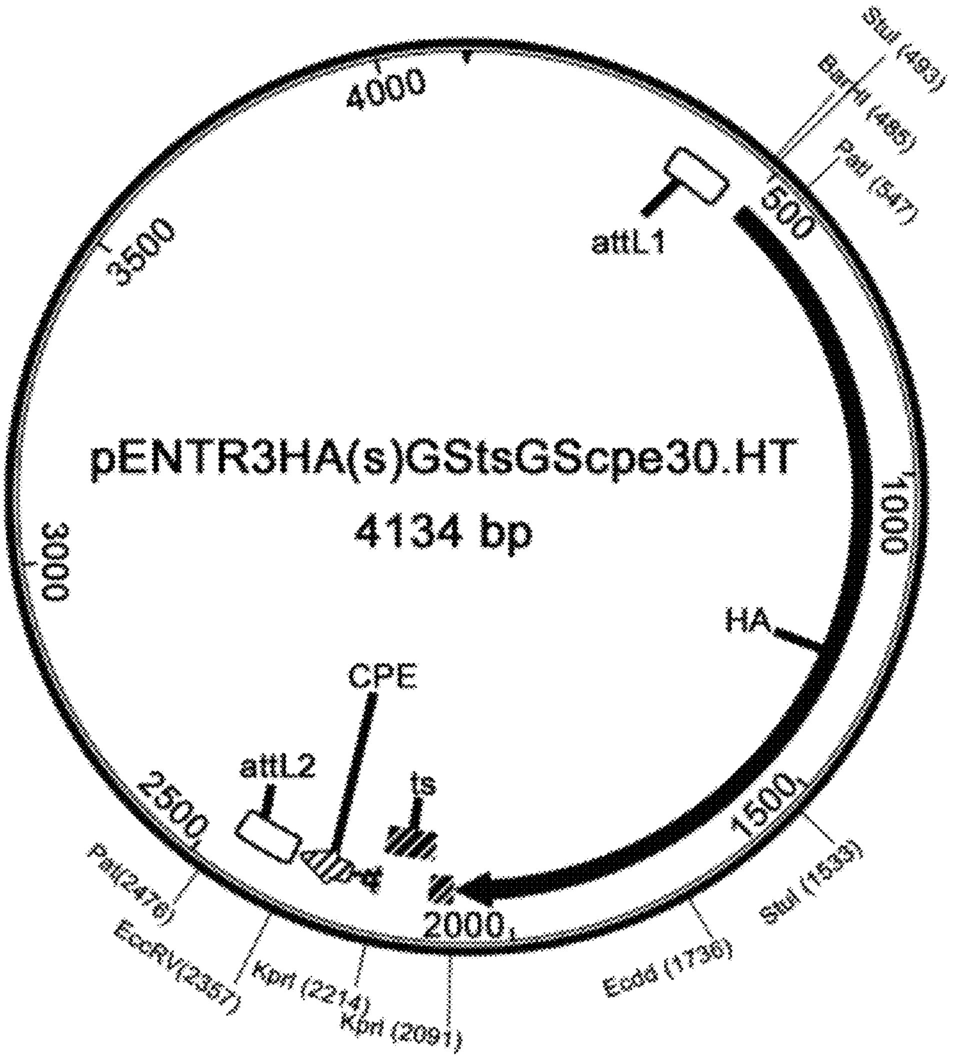

FIG. 9 shows a vector map of the HA-ts-Cpe30-HT expression construct.

Figure 10:
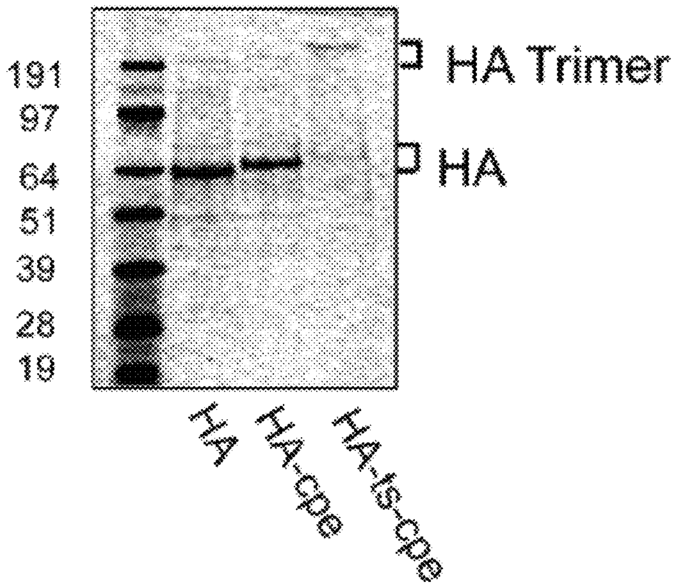

FIG. 10 shows recombinant vaccine antigen production. A truncated influenza hemagglutinin (HA) was produced in baculovirus cultures as HA, HA plus the claudin 4 targeting Cpe30 fusion (HA-cpe), or as HA-cpe with the addition of a trimerization peptide and spacer peptides between the HA and the C-terminal cpe30 peptide (HA-ts-cpe) as shown in FIG. 3. Note the stabilization of the high molecular weight trimer by the trimerization peptide.

Figure 11:
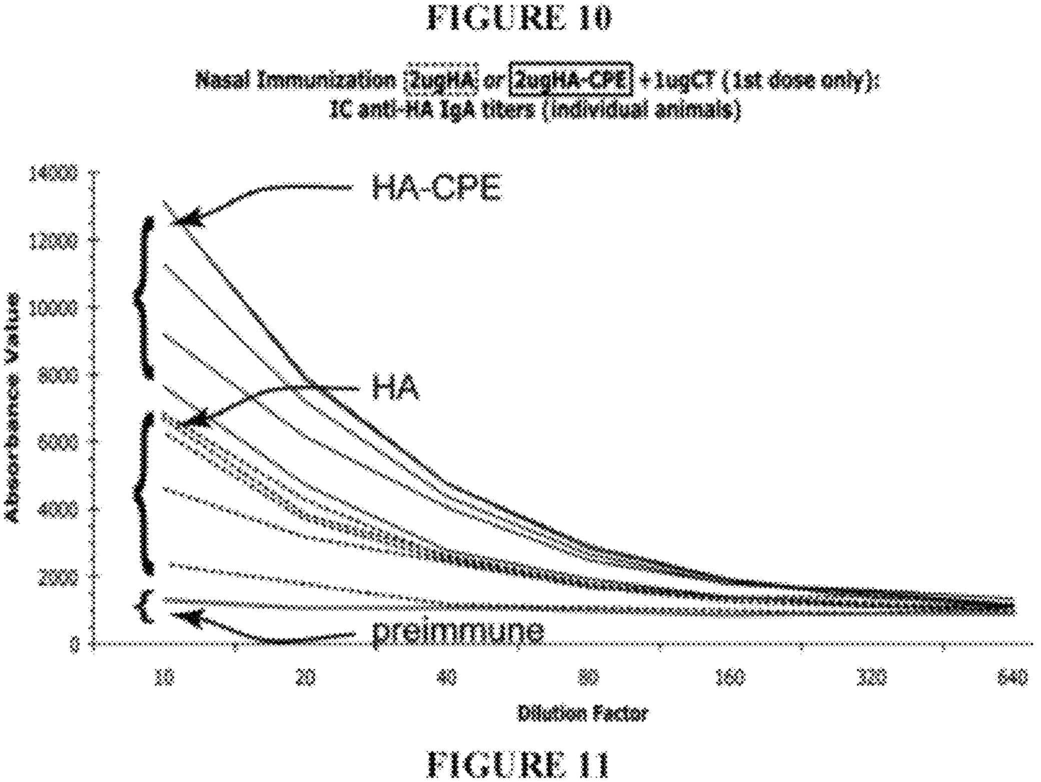

FIG. 11 shows antibody titers in Intestinal Contents (IC) from mucosal immunization. Mice given i.n. 2 ug HA or HA-ts-Cpe30 (3 weekly doses, plus 1 ug cholera toxin with first dose) were tested after four weeks. Serum IgG levels were the same in both groups; titrations from individual animals here shows much higher IgA response in intestinal contents of mice immunized with HA-is-Cpe30 as compared with HA-immunized or naïve animals.

Figure 12:
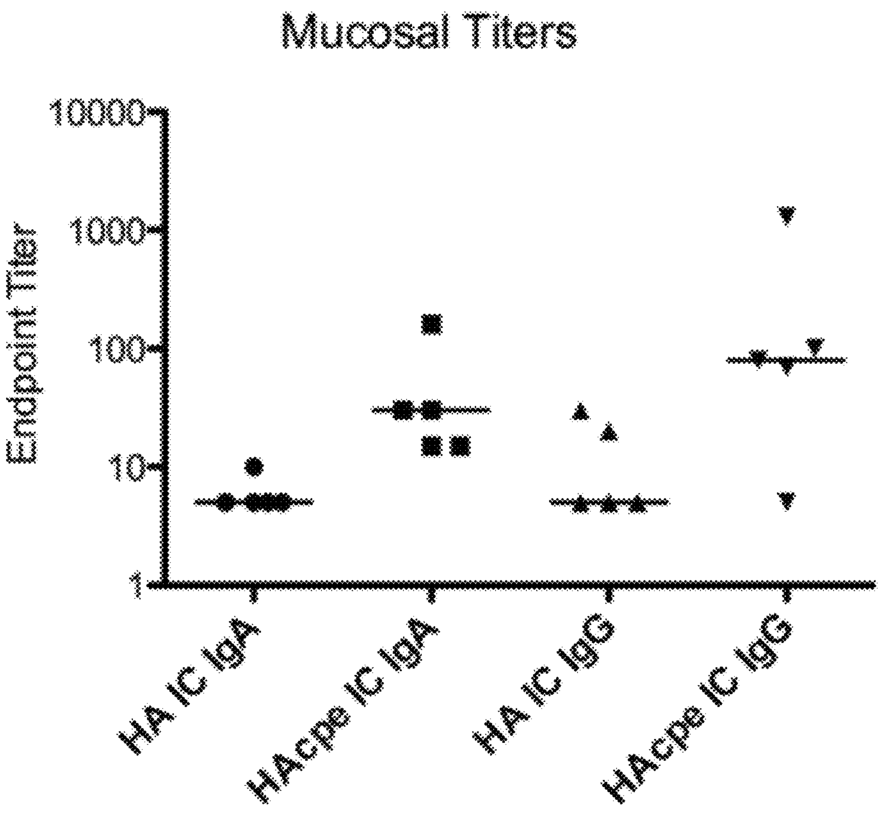

FIG. 12 shows mucosal and serum titers from mucosal immunization. Targeted HA-Cpe30 conjugate (HAcpe) versus HA (with control peptide: a scrambled peptide sequence) as described in the text was used for intranasal immunization. Both intestinal and serum IgA and IgG titers were higher in the M cell targeted vaccine. Bars show median endpoint titer values. Significant differences between HA and HACpe groups were calculated for IgA titers in IC ($p<0.01$) and serum ($p<0.05$) by Mann-Whitney two-tailed test.

FIG. 13A-B shows endpoint titers using HACpe plus HA-flgn. Here, mice were given (A) intranasal HA-control peptide conjugate (10 ug) plus free flagellin (5 ug first dose only), versus (B) HA-Cpe30 conjugate (10 ug) plus recombinant HA-flagellin (5 ug, 3 doses). IC and serum IgA titers shown. (*, $p<0.03$ by one-tailed Mann-Whitney test).

Figure 14:
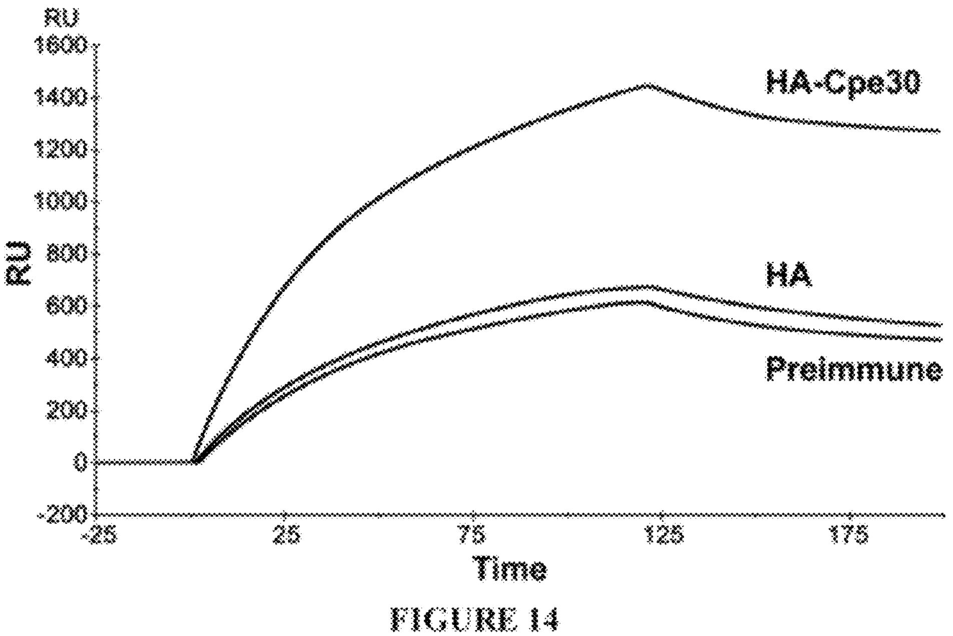

FIG. 14 shows SPR analysis of serum from immunized mice. Equal dilutions of serum from orally immunized mice given HA or HA-CPE30 plus cholera toxin adjuvant. Individual mice are shown here. The HA-CPE30 immunized serum shows higher binding response.

Figure 15:
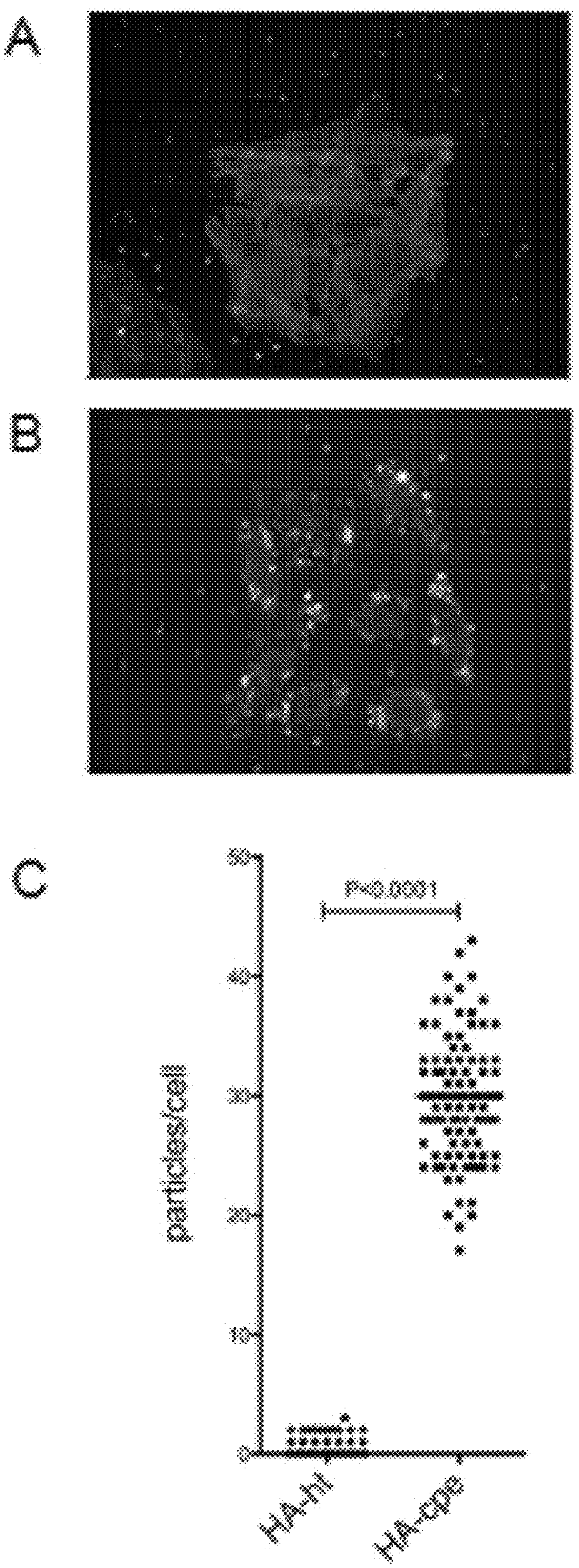

FIG. 15A-C shows in vitro uptake of HA-HT (A) and HA-CPE (B) PLGA nanoparticles: HA-CPE nanoparticles given to GFP-Claudin4 transfectants are readily endocytosed by one hour and colocalize internally with GFP-Claudin4 (bright spots), while HA-HT nanoparticles are not taken up. GFP-Claudin4 (green), Fluorescent nanoparticles (red), nuclei (blue). (C) shows a graph setting out the particle uptake data for PLGA nanoparticles.

Figure 16:
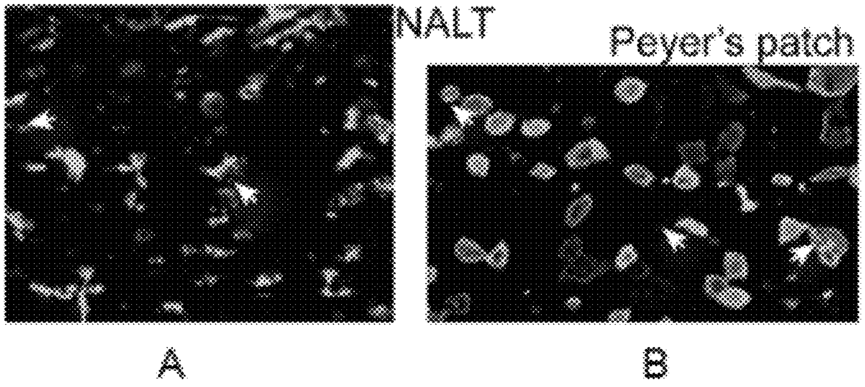

FIG. 16A-B shows uptake of nanoparticles. Fluorescent particles were given either (A) intranasally (NALT) or (B) as oral gavage (Peyer's patch), and tissues were then processed for image analysis. Arrows indicate nanoparticles taken into follicles, though in some cases they are still evident within M cells (green).

Figure 17:
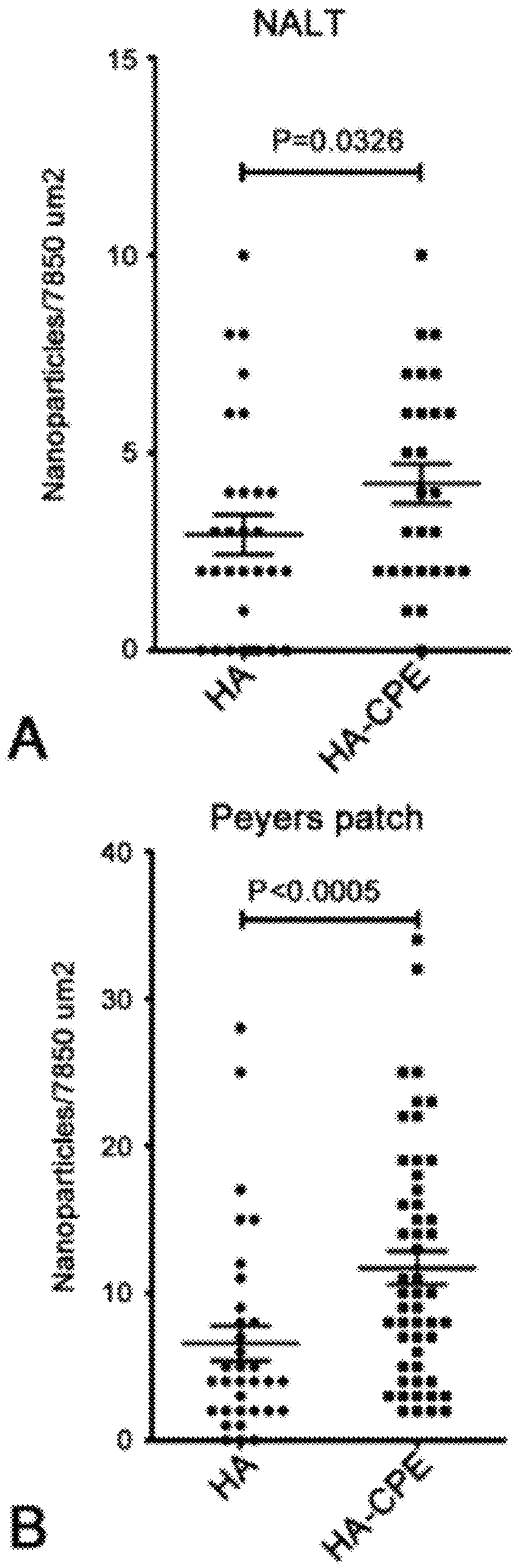

FIG. 17A-B shows uptake of Cpe conjugated particles compared to non-Cpe conjugated particles. Fluorescent nanoparticles were given as an intranasal suspension for 1-2 minutes or intragastric gavage for 4 hours. NALT (A) and Peyer's patch (B) were dissected, fixed and whole mounts were analyzed for fluorescent nanoparticles taken into the lymphoid follicles, measured by particles per circular area (7850 square microns). P values for one tailed Mann-Whitney test shown; data combined from two independent experiments. Note that enhanced uptake mediated by CPE targeting is more evident for Peyer's patch compared to NALT. For comparison, uptake of fluorescent beads conjugated to streptavidin, then coated with biotinylated Cpe30 peptide bound were followed, specific uptake is also evident for these particles as compared to beads coated with a control peptide.

DETAILED DESCRIPTION

As used herein and in the appended claims, the singular forms "a," "and," and "the" include plural referents unless the context clearly dictates otherwise. Thus, for example, reference to "a polynucleotide" includes a plurality of such polynucleotides and reference to "the peptide" includes reference to one or more peptides, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

The Claudin polypeptides are a group of "tetraspan" polypeptides, polypeptides having four membrane-spanning or transmembrane domains that are associated with cellular tight junctions. Claudin family polypeptides are expressed in epithelial cells and/or endothelial cells throughout development, with individual members of the Claudin polypeptide family being expressed in different tissues. The physiological functions associated with a particular Claudin polypeptide are related to the functions performed by the particular tissue(s) in which it is expressed.

Because of their roles in tight junction formation, epithelial and endothelial barrier function, ion transport, and viral protein, enterotoxin, or allergen binding, Claudin polypeptides are associated with conditions involving unregulated or improperly regulated transport across the epithelium or endothelium such as inflammation, asthma, allergy, metastasis of cancer cells, and ion transport disorders such as magnesium transport defects in the kidney. In addition, because a Claudin polypeptide expressed in neural cells has been shown to be required for formation of the myelin sheath in oligodendrocytes, Claudin polypeptides are associated with demyelination conditions such as multiple sclerosis (MS), autoimmune encephalomyelitis, optic neuritis, progressive multifocal leukoencephalopathy (PML), and the like.

Characteristics and activities of the Claudin polypeptide family are described further in the following references: Fujitaab K et al., 2000, *Clostridium perfringens* enterotoxin binds to the second extracellular loop of claudin-3, a tight junction integral membrane protein, FEBS Lett. 476: 258-261; Kinugasa T et al., 2000, Claudins regulate the intestinal barrier in response to immune mediators, Gastroenterology 118: 1001-1011; Tsukita S and Furuse M, 2000, Pores in the wall: claudins constitute tight junction strands containing aqueous pores, J. Cell Biol. 149: 13-16; Bronstein J M et al., 2000, Involvement of OSP/claudin-11 in oligodendrocyte membrane interactions: role in biology and disease, J Neurosci Res. 59: 706-711; Itoh M et al., 1999, Direct binding of three tight junction-associated MAGUKs, ZO-1, ZO-2, and ZO-3, with the COOH termini of claudins, J Cell Biol. 147: 1351-1363; Furuse M et al., 1999, Manner of interaction of heterogeneous claudin species within and between tight junction strands, J Cell Biol. 147: 891-903; Morita K et al., 1999, Endothelial claudin: claudin-5/TMVCF constitutes tight junction strands in endothelial cells, J Cell Biol. 147: 185-194; Kubota K et al., 1999, Ca(2+)-independent cell-adhesion activity of claudins, a family of integral membrane proteins localized at tight junctions, Curr Biol. 9: 1035-1038; Wan H et al., 1999, Der p 1 facilitates transepithelial allergen delivery by disruption of tight junctions, J Clin Invest. 104: 123-133; Simon D B et al., 1999, Paracellin-1, a renal tight junction protein required for paracellular $Mg^{2+}$ resorption, Science 285: 103-106; Morita K et al., 1999, Claudin multigene family encoding four-transmembrane domain protein components of tight junction strands, Proc Natl Acad Sci USA. 96: 511-516; Furuse M et al., 1998, A single gene product, claudin-1 or -2, reconstitutes tight junction strands and recruits occludin in fibroblasts, J Cell Biol. 143: 391-401; Furuse M et al., 1998, Claudin-1 and -2: novel integral membrane proteins localizing at tight junctions with no sequence similarity to occludin, J Cell Biol. 141: 1539-1550; all of which are incorporated by reference herein.

The following shows the coding sequence of human claudin-4, other orthologs and homologs can be identified by performing a routine BLAST search of publicly available databases:

```
                                                        (SEQ ID NO: 11)
  1  atggcctcca tggggctaca ggtaatgggc atcgcgctgg ccgtcctggg ctggctggcc

 61  gtcatgctgt gctgcgcgct gcccatgtgg cgcgtgacgg ccttcatcgg cagcaacatt

121  gtcacctcgc agaccatctg ggagggccta tggatgaact gcgtggtgca gagcaccggc

181  cagatgcagt gcaaggtgta cgactcgctg ctggcactgc cgcaggacct gcaggcggcc

241  cgcgccctcg tcatcatcag catcatcgtg gctgctctgg gcgtgctgct gtccgtggtg

301  gggggcaagt gtaccaactg cctggaggat gaaagcgcca aggccaagac catgatcgtg

361  gcgggcgtgg tgttcctgtt ggccggcctt atggtgatag tgccggtgtc ctggacggcc

421  cacaacatca tccaagactt ctacaatccg ctggtggcct ccgggcagaa gcgggagatg
```

-continued

```
481   ggtgcctcgc tctacgtcgg ctgggccgcc tccggcctgc tgctccttgg cggggggctg
541   ctttgctgca actgtccacc ccgcacagac aagccttact ccgccaagta ttctgctgcc
601   cgctctgctg ctgccagcaa ctacgtgtaa
```

The following shows the amino acid sequence of claudin-4,

```
                                                    (SEQ ID NO: 12)
MASMGLQVMGIALAVLGWLAVMLCCALPMWRVTAFIGSNIVTSQTIWEGL
WMNCVVQSTGQMQCKVYDSLLALPQDLQAARALVIISIIVAALGVLLSVV
GGKCTNCLEDESAKAKTMIVAGVVFLLAGLMVIVPVSWTAHNIIQDFYNP
LVASGQKREMGASLYVGWAASGLLLLGGGLLCCNCPPRTDKPYSAKYSAA
RSAAASNYV
```

As used herein, “Claudin polypeptides” include human Claudin-4 (SEQ ID NO:12) and species homologues and variants and fragments of these Claudin polypeptides. Claudin polypeptides have biological activities and functions that are consistent with those of the other Claudin family polypeptides. Polypeptides of the Claudin family are expressed in cell types including epithelial and endothelial cells throughout development. Typical biological activities or functions associated with this family of polypeptides are tight junction formation, epithelial or endothelial barrier function, ion transport, viral protein binding, homotypic or heterotypic binding, and binding PDZ domain binding. Polypeptides having tight junction formation activity bind to other tight-junction-associated molecules to form tight junction structures that regulate epithelial or endothelial barrier function and paracellular transport. The tight junction formation activity is associated with the extracellular loops and, at least under certain conditions, with the cytoplasmic tail domain of Claudin polypeptides. Thus, for uses requiring tight junction formation activity such polypeptides include those having the extracellular loop domains and exhibiting tight junction formation activities such as epithelial or endothelial barrier function, paracellular ion transport, or viral protein binding. The tight junction formation activity of human Claudin-4 and other Claudin family polypeptides may be determined, for example, by introducing Claudin polypeptides into cells that do not normally form tight junctions, such a L fibroblasts, along with occludin or any other polypeptide that the Claudin polypeptide needs to interact with in the formation of tight junctions, then visualizing the resulting tight junction structures by electron microscopy or immunofluorescence methods (see, for example, Furuse et al., J Cell Biol. 143: 391-401, 1998). Alternatively, the paracellular ion transport activity of human Claudin-4 and other Claudin family polypeptides may be assayed by electrophysiology or through the use of luminescent ion indicator molecules such as aequorin. As described more fully below, such techniques can be used to assess the activity of Claudin-4 binding peptides of the disclosure.

The term “human Claudin polypeptide activity,” as used herein, includes any one or more of the following: tight junction formation, epithelial or endothelial barrier function, and ion transport activity; homotypic binding, heterotypic binding, viral protein binding, enterotoxin binding, and PDZ domain binding activity; as well as the ex vivo and in vivo activities of Claudin polypeptides. The degree to which Claudin polypeptides and fragments and other derivatives of these polypeptides exhibit these activities can be determined by standard assay methods. Exemplary assays are disclosed herein; those of skill in the art will appreciate that other, similar types of assays can be used to measure the biological activities of Claudin polypeptides and other Claudin family members.

One aspect of the biological activity of Claudin polypeptides including human Claudin-4 is the ability of members of this polypeptide family to bind particular binding partners such homotypic and heterotypic polypeptides, viral proteins, enterotoxins, and PDZ-domain-containing polypeptides, with the extracellular loop domains binding, for example, to homotypic polypeptides, and the cytoplasmic tail domain binding to PDZ-domain-containing polypeptides.

The term “binding partner,” as used herein, includes peptides that interacts with a Claudin-4 polypeptide through contact or proximity between particular portions of the binding partner and the Claudin-4 polypeptide. The interactions between Claudin polypeptides and binding partners are involved in mediating interactions between adjacent epithelial cells, and interactions between adjacent endothelial cells. Artificial binding peptide or domains (including soluble domains) of the disclosure either alone or in a fusion construct or polypeptide (e.g., fused to an immunoglobulin Fc domain, an immunogenic molecule, a nanoparticle or the like), is expected to disrupt the binding of Claudin polypeptides to their normal binding partners or facilitate uptake by a desired cell expressing claudin-4.

Polypeptides of the Claudin family are involved in epithelial or endothelial barrier function and transport diseases or conditions that share as a common feature of abnormal tight junction formation or improperly regulated tight junction function (i.e. abnormal epithelial or endothelial barrier function) in their etiology. More specifically, the following conditions involving epithelial or endothelial barrier function and/or binding to Claudin polypeptides are those that are known or are likely to involve the biological activities of Claudin polypeptides: inflammation (e.g., psoriasis and other inflammatory dermatoses), asthma, allergy, cell proliferative disorders (e.g., hyperproliferative skin disorders including skin cancer), metastasis of cancer cells, ion transport disorders such as magnesium transport defects in the kidney, inflammatory bowel disease, and exposure to *Clostridium perfringens* enterotoxin (CPE). In addition, because a Claudin polypeptide expressed in neural cells has been shown to be required for formation of the myelin sheath in oligodendrocytes, Claudin polypeptides are associated with demyelination conditions such as multiple sclerosis (MS), autoimmune encephalomyelitis, optic neuritis, and progressive multifocal leukoencephalopathy (PML). Also, diseases that are promoted by one or more of the conditions above may involve Claudin polypeptides, directly or indirectly. For example, susceptibility to sudden infant death syndrome (SIDS) has been associated with exposure to CPE. Blocking or inhibiting the interactions between a claudin-4 polypeptide and their substrates, ligands, receptors and or other interacting polypeptides is provided by the disclosure and provides methods for treating or ameliorating these diseases and conditions through the use of inhibitors of human Claudin-4 activity. Examples of such inhibitors or antagonists are described in more detail below. Additional uses for Claudin binding peptides include diagnostic reagents for epithelial or endothelial transport diseases; research reagents for investigation or as a carrier or targeting molecule for the delivery of therapeutic agents or diagnostic agents, particularly in view of the role of Claudins in the tight junctions.

The disclosure also provides compositions and methods for mucosal delivery of therapeutics, diagnostics and biologically active peptides and proteins. For example, a therapeutic moiety (e.g., an immunogenic polypeptide, small molecule drug or diagnostic agent) can be linked to a binding peptide of the disclosure and delivered to a cell or subject, wherein the binding peptide selectively binds to a claudin polypeptide (e.g., a claudin-4 polypeptide). Because claudins are normally expressed on endothelial and epithelial cells, the binding peptide will interact with such cells in mucosal tissues thereby delivery any linked payload to the tissue or cell. Useful agents that can be linked to a binding peptide of the disclosure include, for example, tissue plasminogen activator (TPA), epidermal growth factor (EGF), fibroblast growth factor (FGF-acidic or basic), platelet derived growth factor (PDGF), transforming growth factor (TGF-alpha or beta), vasoactive intestinal peptide, tumor necrosis factor (TNF), hypothalmic releasing factors, prolactin, thyroid stimulating hormone (TSH), adrenocorticotropic hormone (ACTH), parathyroid hormone (PTH), follicle stimulating hormone (FSF), luteinizing hormone releasing hormone (LHRH), endorphins, glucagon, calcitonin, oxytocin, carbetocin, aldoetecone, enkaphalins, somatostin, somatotropin, somatomedin, gonadotrophin, estrogen, progesterone, testosterone, alpha-melanocyte stimulating hormone, non-naturally occurring opiods, lidocaine, ketoprofen, sufentainil, terbutaline, droperidol, scopolamine, gonadorelin, ciclopirox, olamine, buspirone, calcitonin, cromolyn sodium or midazolam, cyclosporin, lisinopril, captopril, delapril, cimetidine, ranitidine, famotidine, superoxide dismutase, asparaginase, arginase, arginine deaminease, adenosine deaminase ribonuclease, trypsin, chemotrypsin, and papain. Additional examples of useful peptides include, but are not limited to, bombesin, substance P, vasopressin, alpha-globulins, transferrin, fibrinogen, beta-lipoproteins, beta-globulins, prothrombin, ceruloplasmin, alpha$_2$-glycoproteins, alpha$_2$-globulins, fetuin, alpha1-lipoproteins, alpha1-globulins, albumin, prealbumin, and other bioactive proteins and recombinant protein products.

The disclosure also provides methods and compositions for providing mucosal delivery of specific, biologically active peptide, protein or small molecule therapeutics to treat (i.e., to eliminate, or reduce the occurrence or severity of symptoms of) an existing disease or condition, or to prevent onset of a disease or condition in a subject identified to be at risk for the subject disease or condition. Biologically active molecules that are useful include, but are not limited to, cytokines; immunopotentiating agents; growth factors; hormones; hematopoietics; antiinfective agents; antidementia agents; antiviral agents; antitumoral agents; antipyretics; analgesics; antiinflammatory agents; antiulcer agents; antiallergic agents; antidepressants; psychotropic agents; cardiotonics; antiarrythmic agents; vasodilators; antihypertensive agents such as hypotensive diuretics; antidiabetic agents; anticoagulants; cholesterol lowering agents; therapeutic agents for osteoporosis; hormones; antibiotics; vaccines; and the like. Exemplary hormones include androgens, estrogens, prostaglandins, somatotropins, gonadotropins, interleukins, steroids and cytokines.

Furthermore, vaccines which may be administered within the methods and compositions of the disclosure include bacterial and viral vaccines, such as vaccines for hepatitis, influenza, Dengue, rotavirus, vibrio, SARS, respiratory syncytial virus (RSV), parainfluenza virus (PIV), tuberculosis, canary pox, chicken pox, measles, mumps, rubella, pneumonia, and human immunodeficiency virus (HIV). For example, HA antigens can be linked to a binding peptide of the disclosure and used for immunization. Bacterial toxoids can be used with the methods and compositions disclosure including, for example, diphtheria, tetanus, pseudonomas and mycobactrium tuberculosis.

Conventional vaccine development has been mainly based on either infection with an attenuated pathogen, or direct subcutaneous or intramuscular injection of inert antigens from the pathogen. The attenuated pathogen, if available, provides a persistent stimulus similar to the pathogenic infection. Here, an effective immune response may be generated in the regional site most appropriate for protective immunity, but attenuated strains are often not available or they risk causing the infectious disease itself. By contrast, direct injection of antigen predominantly induces a systemic IgG response. While this may be adequate in many cases, it is acknowledged to be less effective in providing regional immunity.

Thus, in mucosal tissues, secretory IgA responses provide the best protective response. For respiratory pathogens, secretory IgA is of obvious benefit, as it is secreted at very high levels onto mucosal surfaces, where it can neutralize viral pathogens and prevent either direct infection of epithelial cells or entry across the epithelial barrier. However, immunization for mucosal responses has additional benefits to the patient; while systemic immunization can provide only systemic (serum) IgG responses, mucosal immunization induces both serum IgG and mucosal IgA responses. Moreover, IgA: virus immune complexes can be transcytosed by the pIgR intact across the mucosal epithelium into the intestinal lumen for eventual elimination, thereby potentially providing both protection from mucosal infections and active elimination of infectious particles that are already in the body, as in the case of blood-borne infections.

Surprisingly, vaccine development efforts have not yet taken advantage of the additional practical advantages of mucosal immunization. Administration of vaccines targeted to the mucosal immune tissues could be done relatively cheaply and easily; with oral or intranasal delivery not requiring needles for injections, trained medical staff, and specialized equipment. This principle has been recognized in many mouse studies using methods to target delivery of vaccine antigens to mucosal M cells in the follicle epithelium overlying lymphoid tissues such as Peyer's Patches. M cells are specialized for particle transcytosis from the intestinal lumen to the lymphoid follicle, but to date the targeting of vaccines to M cells has relied only on targets unique to mouse and not present on human M cells. What is needed therefore is a method for targeting vaccine delivery to the mucosal immune system that uses targets shared by both mouse and human.

For example, M cells are specialized epithelial cells found mainly overlying lymphoid follicles such as Nasopharyngeal Associated Lymphoid Tissue (NALT) in the mouse, tonsils in the human, and Peyer's Patches in both species. M cells are specialized for antigen and particle uptake and transcytosis to the basolateral side of the Peyer's Patch Follicle Associated Epithelium (PPFAE), or NALT epithelium, where waiting antigen presenting cells take up the antigens for presentation to follicle lymphocytes and stimulate IgA responses. The redistribution of cldn4 in M cells in vivo from tight junctions to the cytoplasm in both mouse and human Peyer's Patches shows that this transmembrane protein participates in particle transcytosis. In support of this hypothesis, lymphotoxin/TNF treatment of the human intestinal epithelium cell line Caco-2BBe also induced redistribution of cldn4 and that many of the bacteria were found within cldn4-positive vesicles when these cells were allowed to endocytose fluorescently labeled bacterial particles. These results implicate cldn4 as a component of M cell transcytosis. As demonstrated herein, the targeting of extracellular domains of cldn4 mediate efficient delivery of vaccine antigens to mucosal lymphoid tissue.

The redistribution of cldn4 in M cells in vivo from tight junctions to the cytoplasm in both mouse and human Peyer's Patches demonstrates that this transmembrane protein might participate in particle transcytosis. In support of this hypothesis, the disclosure demonstrates that lymphotoxin/TNF treatment of the human intestinal epithelium cell line Caco-2BBe also induced redistribution of cldn4 and that many of the bacteria were found within cldn4-positive vesicles when these cells were allowed to endocytose fluorescently labeled bacterial particles. These results implicated cldn4 as a component of M cell transcytosis. The disclosure also demonstrates that targeting of extracellular domains of cldn4 mediate efficient delivery of vaccine antigens to mucosal lymphoid tissue.

The disclosure demonstrates the use of short peptides for targeting vaccine antigens to M cells. These peptides are easily incorporated into recombinant vaccine antigens as fusion proteins, so that a single process could generate both antigen and delivery "vehicle." Adjuvants can further be used in the delivery compositions and methods. The disclosure shows that *Clostridium perfringens* enterotoxin (Cpe), a ligand for cldn4 can be used in the methods and compositions of the disclosure (as described herein). These targeting peptides can be shown to have a direct effect on delivery of "packages" to mucosal lymphoid tissues.

The disclosure provides claudin-4 binding peptides capable of interacting with a claudin-4. Such peptides are typically between about 8 and about 50 amino acids (e.g., 9, 10, 11, 12, 13, 14, 15, 16, 17, 18, 19, 20, 21, 22, 23, 24, 25, 26, 27, 28, 29, and 30 or more amino acids). In one embodiment, the disclosure provides a substantially purified peptide comprising from about 8-30 amino acids and containing a tyrosine or tryptophan separated by 3-4 amino acids followed by 1 or 2 tyrosines and a leucine. In another embodiment, the peptide comprises about 8 to 30 amino acids and comprising the amino acid sequence (Y/W)$(Xaa)_{3\ or\ 4}$ YYXaaL (SEQ ID NO:1) wherein Xaa is any amino acid. In yet another embodiment, the disclosure provides a peptide comprising a sequence of between 10-30 amino acids containing a sequence of (Y/W)$(Xaa)_{3\ or\ 4}$ YYXaaL (SEQ ID NO:1). In one embodiment, the peptide comprises a sequence XaaXaaXaaXaa(Y/W)$(Xaa)_{3\ or\ 4}$ YYXaaL (SEQ ID NO:2). In another embodiment, the peptide comprises a sequence XaaXaa(Y/W)$(Xaa)_{3\ or\ 4}$Y(Y/Xaa)(L/I)XaaXaa (SEQ ID NO:3). In specific embodiment, the peptide is selected from the group consisting of: SLDAGQYVLVMKANSSYSGNYPYSILFQKF (SEQ ID NO:4), NSSYSGNYPYSILFQKF (SEQ ID NO:5), SSYSGNYPYSIL (SEQ ID NO:6), NSSYSGNYYSIL (SEQ ID NO:7), ASNSSYSGNYSIL (SEQ ID NO:8), SPWSEPAYTLAP (SEQ ID NO:9), and APWTEHSYYLSL (SEQ ID NO:10). In yet another embodiment, the peptide comprises at least one D-amino acid. In a further embodiment, the peptide binds to a claudin-4. In another aspect, the peptide comprises a sequence as set forth in Table 1.

Peptides of the disclosure can be synthesized by commonly used methods such as those that include t-BOC or FMOC protection of alpha-amino groups. Both methods involve stepwise synthesis in which a single amino acid is added at each step starting from the C-terminus of the peptide (See, Coligan, et al., Current Protocols in Immunology, Wiley Interscience, 1991, Unit 9). Peptides of the disclosure can also be synthesized by the well known solid phase peptide synthesis methods such as those described by Merrifield, J. Am. Chem. Soc., 85:2149, 1962; and Stewart and Young, Solid Phase Peptides Synthesis, Freeman, San Francisco, 1969, pp. 27-62) using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with a 1% acetic acid solution, which is then lyophilized to yield the crude material. The peptides can be purified by such techniques as gel filtration on Sephadex G-15 using 5% acetic acid as a solvent. Lyophilization of appropriate fractions of the column eluate yield homogeneous peptide, which can then be characterized by standard techniques such as amino acid analysis, thin layer chromatography, high performance liquid chromatography, ultraviolet absorption spectroscopy, molar rotation, or measuring solubility. If desired, the peptides can be quantitated by the solid phase Edman degradation.

A polypeptide and peptide comprise a polymer in which the monomers are amino acid residues which are joined together through amide bonds. When the amino acids are alpha-amino acids, either the L-optical isomer or the D-optical isomer can be used. A polypeptide encompasses an amino acid sequence and includes modified sequences such as glycoproteins, retro-inverso polypeptides, D-amino acid modified polypeptides, and the like. A polypeptide includes naturally occurring proteins, as well as those which are recombinantly or synthetically synthesized. "Fragments" are a portion of a polypeptide. The term "fragment" refers to a portion of a polypeptide which exhibits at least one useful epitope or functional domain. The term "functional fragment" refers to fragments of a polypeptide that retain an activity of the polypeptide. For example, a functional fragment of a binding peptide of the disclosure includes a fragment which retains the ability to bind to a claudin family polypeptide such as claudin 4. Biologically functional fragments, for example, can vary in size from a polypeptide fragment as small as an epitope capable of binding an antibody molecule, to a large polypeptide.

In some embodiments, retro-inverso peptides are used. "Retro-inverso" means an amino-carboxy inversion as well as enantiomeric change in one or more amino acids (i.e., levantory (L) to dextrorotary (D)). A polypeptide of the disclosure encompasses, for example, amino-carboxy inversions of the amino acid sequence, amino-carboxy inversions containing one or more D-amino acids, and non-inverted sequence containing one or more D-amino acids. Retro-inverso peptidomimetics that are stable and retain bioactivity can be devised as described by Brugidou et al. (Biochem. Biophys. Res. Comm. 214(2): 685-693, 1995) and Chorev et al. (Trends Biotechnol. 13(10): 438-445, 1995). The overall structural features of a retro-inverso polypeptide are similar to those of the parent L-polypeptide. The two molecules, however, are roughly mirror images because they share inherently chiral secondary structure elements. Main-chain peptidomimetics based on peptide-bond reversal and inversion of chirality represent important structural alterations for peptides and proteins, and are highly significant for biotechnology. Antigenicity and immunogenicity can be achieved by metabolically stable antigens such as all-D-and retro-inverso-isomers of natural antigenic peptides.

In another embodiment, the peptide is produced by recombinant DNA techniques. For example, an oligonucleotide or polynucleotide encoding a peptide of the disclosure can be expressed from an expression vector and the resulting peptide purified using techniques known in the art (e.g., HPLC or other chromtography techniques). The produced pepetides may be substantially purified and used in methods of the disclosure or they may be substantially purified and conjugated to a second molecule of interest. Exemplary molecules include polypeptides or peptide (e.g., such as a growth factor, vaccine or immunogen, antibody and the like); small molecule drugs or nano-, micro-particles. Such nano-and micro-particles are useful in diagnostic assays, drug delivery, and therapeutics. For example, nano-and micro-particles can be used for imaging, or heating a cancer tissue to induce cell destruction.

Suitable nanoparticles are commercially available and include hollow-and solid-nano-spheres, -cubes, -bowls, -rods, and -porous structures. In some embodiments, the nanostructure will comprise a noble metal (e.g., Ag, Au, Pt) or a combination of noble metals and may further include a magnetic metal. Methods of conjugating a peptide of the disclosure to a nanoparticle are known in the art and include alkanethiol linkages and the like. The signature of a noble metal nanostructure is the localized surface plasmon resonance. This resonance occurs when the correct wavelength of electromagnetic energy (e.g., light) strikes a noble metal nanostructure causing the plasma of conduction electrons to oscillate collectively. The resonance oscillation is localized near the surface region of the nanostructure. Such resonance is advantageous in that the nanostructure is selectively excited at a particular photon absorption, which results in the generation of locally enhanced or amplified electromagnetic fields at the nanostructure surface. The resonance for noble metal nanostructures (e.g., in the 20-500 nm range) occurs in the visible and IR regions of the spectrum and can be measured by UV-visible-IR extinction spectroscopy. In some nanostructures, the nanostructure can be tuned to generate a particular absorbance and emission spectra by adjusting the metallic composition and geometry.

A peptide of the disclosure useful for targeting the nanostructure to an endothelial or epithelial tissue or cell may be conjugated to the nanostructure by any number of techniques. The peptide may also be linked (or the nanostructure linked) to a second polypeptide comprising a desired small molecule drug or polypeptide.

The nanostructures may be functionalized. The term "functionalized" is meant to include structures with two or more layers of different metals, structures with functional groups attached thereto, structures that have optical properties, magnetic structures, etc. The nanostructures of can optionally be functionalized by imprinting functional groups, such as antibodies, proteins, nucleic acids, and the like. Such nanostructures are particularly useful for molecular diagnostics. For example, to prolong or target analyte interaction with the noble metal nanoparticle surface, a binding agent/targeting domain is used to promote interaction of a nanostructure with a desired target. In one embodiment, the nanostructure is functionalized with a peptide of the disclosure that interacts with a claudin-4. In one embodiment, the functionalized nanostructure comprising a claudin-4 binding peptide is useful for targeted delivery to an endothelial or epithelial cell or tissue. An alkanethiol, such as 1-decanethiol, can be used to form the capture layer on the noble metal (Blanco Gomis et al., J. Anal. Chim. Acta 436:173 [2001]; Yang et al., Anal. Chem. 34:1326 [1995]). Other exemplary capture molecules include longer-chained alkanethiols, cyclohexyl mercaptan, glucosamine, boronic acid and mercapto carboxylic acids (e.g., 11-mercaptoundecanoic acid).

Alternatively, a self-assembled monolayer (SAM) is formed on the nanostructure surface to concentrate the analyte of interest near the surface of the nanostructure. Exemplary SAMs include, but are not limited to, 4-aminothiophenol, L-cystein, 3-mercaptopropionicacid, 11-mercaptoundecanoic acid, 1-hexanethiol, 1-octanethiol, 1-DT, 1-hexadecanethiol, poly-DL-lysine, 3-mercapto-1-propanesufonic acid, benzenethiol, and cyclohexylmercaptan. Typically the SAM is comprised of straight chain alkanethiols.

As described above, a targeting ligand (e.g., a binding peptide) can include a claudin-4 binding peptide bound to the surface of a nanostructure such that the nanostructure interacts reversibly or irreversibly with a specific analyte. Typically, the interaction of the targeting ligand and the analyte lasts sufficiently long for detection of the analyte by SERS or to promote uptake and delivery of an attached payload.

In one embodiment, nanoparticles may be formed from compatible polymers and biomaterials such as poly(lactide-co-glycolide) (PLGA), poly(lactide) (PLA), poly $\epsilon$-caprolactone, albumin, and chitosan. In certain embodiments, the carrier particles are formed from the biodegradable polymers PLGA or PLA. PLGA and PLA are able to control the release of bioactive macromolecules (e.g., therapeutic agents). PLGA is a well-studied polymer for drug delivery and is FDA-approved for a number of in vivo applications. PLGA degradation times can be varied from days to years by altering the type of polymer, the polymer molecular weight, or the structure of the nanospheres. Further, modifying the end groups of PLGA with acid groups (COOH) allows for greater conjugation of peptide or protein molecules thereby allowing the nanoparticles to be targeted to specific cell types.

In some embodiments, the carrier particles are associated with a therapeutic agent (e.g., the therapeutic agent is entangled, embedded, incorporated, encapsulated, bound to the surface, or otherwise associated with the carrier particle). In certain embodiments, the therapeutic agent is a drug such as a pure drug (e.g., drugs processed by crystallization or supercritical fluids), an encapsulated drug (e.g., polymers), a surface associated drug (e.g., drugs that are adsorbed or bound to the carrier particle surface), a complexed drug (e.g., drugs that are associated with the material used to form the carrier particle). In a different embodiment, the carrier particles exhibit fluorescent activity or a measurable signal when exposed to light or another external stimulus, which is useful for diagnostics, imaging and sensoring.

The carrier particles of the disclosure, in certain embodiments, do not include a functional group. In other aspects, however, the carrier particles can include a functional group such as, for example, a carboxyl, sulfhydryl, hydroxyl, or amino group, or any other functional group that can be used to bind a targeting moiety or moieties to the surface of the carrier particles.

The carrier particles may be formed by suitable means known in the art, for example microspheres may be formed as described in U.S. Pat. No. 7,083,572, and nanoparticles may be formed as described in U.S. Pat. No. 6,632,671. It is also known in the art how to incorporate or encapsulate one or more therapeutic agents in the carrier particles for delivery. Large porous particles may be prepared using conventional techniques such as spray drying or emulsion solvent evaporation, or through supercritical fluid derived processes such as those described by Koushik & Kompella (2004) Pharm. Res. 21:524-35.

In specific embodiments, a PLGA micro-or nano-particle is linked to a claudin-4 binding peptide to promote targeting to endothelial and epithelial tissues. The PLGA may have incorporated thereon or therein a therapeutic agent such as a vaccine or small molecule drug.

In another aspect, the disclosure provides a method of producing a fusion polypeptide comprising a binding peptide domain and a heterologous molecule by growing a host cell comprising a polynucleotide encoding the fusion polypeptide under conditions that allow expression of the polynucleotide, and recovering the fusion polypeptide. A polynucleotide encoding a fusion polypeptide of the disclosure can be operably linked to a promoter for expression in a prokaryotic or eukaryotic expression system. For example, such a polynucleotide can be incorporated in an expression vector. In addition, fusion polypeptide may be generated comprising two coding domains operably linked in-frame such that upon expression both domains retain a functional activity. For example, a useful fusion construct of the disclosure comprises a coding sequence for a claudin-4 binding peptide of the disclosure operably linked (e.g., directly or via a linker) to a peptide or polypeptide of interest. Such a peptide or polypeptide of interest can be a growth factor, antibody, immunogenic peptide or polypeptide molecule and the like.

Delivery of a polynucleotide of the disclosure can be achieved by introducing the polynucleotide into a cell using a variety of methods known to those of skill in the art. For example, a construct comprising such a polynucleotide can be delivered into a cell using a colloidal dispersion system. Alternatively, a polynucleotide construct can be incorporated (i.e., cloned) into an appropriate vector. For purposes of expression, the polynucleotide encoding a fusion polypeptide of the disclosure may be inserted into a recombinant expression vector. The term "recombinant expression vector" refers to a plasmid, virus, or other vehicle known in the art that has been manipulated by insertion or incorporation of a polynucleotide encoding a fusion polypeptide of the disclosure. The expression vector typically contains an origin of replication, a promoter, as well as specific genes that allow phenotypic selection of the transformed cells. Vectors suitable for such use include, but are not limited to, the T7-based expression vector for expression in bacteria (Rosenberg et al., Gene, 56:125, 1987), the pMSXND expression vector for expression in mammalian cells (Lee and Nathans, J. Biol. Chem., 263:3521, 1988), baculovirus-derived vectors for expression in insect cells, cauliflower mosaic virus, CaMV, and tobacco mosaic virus, TMV, for expression in plants.

Depending on the vector utilized, any of a number of suitable transcription and translation elements (regulatory sequences), including constitutive and inducible promoters, transcription enhancer elements, transcription terminators, and the like may be used in the expression vector (see, e.g., Bitter et al., Methods in Enzymology, 153:516-544, 1987). These elements are well known to one of skill in the art.

The term "operably linked" or "operably associated" refers to functional linkage between the regulatory sequence and the polynucleotide regulated by the regulatory sequence. The operably linked regulatory sequence controls the expression of the product expressed by the polynucleotide. The term "operably linked" also include linking of two heterologous or homologous domains through a linker or other moiety such that each domain is functional.

In yeast, a number of vectors containing constitutive or inducible promoters may be used. (Current Protocols in Molecular Biology, Vol. 2, Ed. Ausubel et al., Greene Publish. Assoc. & Wiley Interscience, Ch. 13, 1988; Grant et al., "Expression and Secretion Vectors for Yeast," in Methods in Enzymology, Eds. Wu & Grossman, Acad. Press, N.Y., Vol. 153, pp. 516-544, 1987; Glover, DNA Cloning, Vol. II, IRL Press, Wash., D.C., Ch. 3, 1986; "Bitter, Heterologous Gene Expression in Yeast,"Methods in Enzymology, Eds. Berger & Kimmel, Acad. Press, N.Y., Vol. 152, pp. 673-684, 1987; and The Molecular Biology of the Yeast Saccharomyces, Eds. Strathern et al., Cold Spring Harbor Press, Vols. I and II, 1982). A constitutive yeast promoter, such as ADH or LEU2, or an inducible promoter, such as GAL, may be used ("Cloning in Yeast," Ch. 3, R. Rothstein In: DNA Cloning Vol. 11, A Practical Approach, Ed. D M Glover, IRL Press, Wash., D.C., 1986). Alternatively, vectors may be used which promote integration of foreign DNA sequences into the yeast chromosome.

An expression vector can be used to transform a target cell. By "transformation" is meant a permanent genetic change induced in a cell following incorporation of a polynucleotide exogenous to the cell. Where the cell is a mammalian cell, a permanent genetic change is generally achieved by introduction of the polynucleotide into the genome of the cell. By "transformed cell" is meant a cell into which (or into an ancestor of which) has been introduced, by means of molecular biology techniques, a polynucleotide encoding a fusion polypeptide comprising a binding peptide linked to a heterologous polypeptide or fusogenic polypeptide. Transformation of a host cell may be carried out by conventional techniques as are known to those skilled in the art. Where the host is prokaryotic, such as *E. coli,* competent cells which are capable of polynucleotide uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

A fusion polypeptide of the disclosure can be produced by expression of polynucleotide encoding a fusion polypeptide in prokaryotes. These include, but are not limited to, microorganisms, such as bacteria transformed with recombinant bacteriophage DNA, plasmid DNA, or cosmid DNA expression vectors encoding a fusion polypeptide of the disclosure. The constructs can be expressed in *E. coli* in large scale for in vitro assays. Purification from bacteria is simplified when the sequences include tags for one-step purification by nickel-chelate chromatography. Thus, a polynucleotide encoding a fusion polypeptide can also comprise a tag to simplify isolation of the fusion polypeptide. For example, a polyhistidine tag of, e.g., six histidine residues, can be incorporated at the amino terminal end of the fusion polypeptide. The polyhistidine tag allows convenient isolation of the protein in a single step by nickel-chelate chromatography. A fusion polypeptide of the disclosure can also be engineered to contain a cleavage site to aid in protein recovery or other linker moiety separating a binding peptide from a heterologous molecule (e.g., an immunogenic/vaccine polypeptide or peptide). Typically a linker will be a peptide linker moiety. The length of the linker moiety is chosen to optimize the biological activity of the polypeptide comprising binding peptide domain and a heterologous molecule and can be determined empirically without undue experimentation. The linker moiety should be long enough and flexible enough to allow a binding peptide polypeptide to freely interact. A linker moiety is a peptide between about one and 30 amino acid residues in length, typically between about two and 15 amino acid residues. Examples of linker moieties are -Gly-Gly-, GGGGS (SEQ ID NO:13) one or more times, GKSSGSGSESKS (SEQ ID NO:14), GSTSGSGKSSEGKG (SEQ ID NO:15), GSTSGSGKSSEGSGSTKG (SEQ ID NO:16), GSTSGSGKPGSGEGSTKG (SEQ ID NO:17), or EGKSSGSGSESKEF (SEQ ID NO:18). Linking moieties are described, for example, in Huston et al., Proc. Nat'l Acad. Sci 85:5879, 1988; Whitlow et al., Protein Engineering 6:989, 1993; and Newton et al., Biochemistry 35:545, 1996. Other suitable peptide linkers are those described in U.S. Pat. Nos. 4,751,180 and 4,935,233, which are hereby incorporated by reference. A DNA sequence encoding a desired peptide linker can be inserted between, and in the same reading frame as, a polynucleotide encoding a claudin-4 binding peptide or fragment thereof followed by a heterologous polypeptide, using any suitable conventional technique. For example, a chemically synthesized oligonucleotide encoding the linker can be ligated between two coding polynucleotides. In particular embodiments, a fusion polypeptide comprises from two to four separate domains (e.g., a binding peptide domain and a heterologous polypeptide domain) are separated by peptide linkers.

When the host is a eukaryote, such methods of transfection of DNA as calcium phosphate co-precipitates, conventional mechanical procedures, such as microinjection, electroporation, insertion of a plasmid encased in liposomes, or virus vectors may be used. Eukaryotic cells can also be cotransfected with a polynucleotide encoding the binding peptide-fusion polypeptide of the disclosure, and a second polynucleotide molecule encoding a selectable phenotype, such as the herpes simplex thymidine kinase or cytosine deaminase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982).

Eukaryotic systems, and typically mammalian expression systems, allow for proper post-translational modifications of expressed mammalian proteins to occur. Eukaryotic cell s that possess the cellular machinery for proper processing of the primary transcript, glycosylation, phosphorylation, and advantageously secretion of the gene product can be used as host cells for the expression of the binding peptide-fusion polypeptide of the disclosure. Such host cell lines may include, but are not limited to, CHO, VERO, BHK, HeLa, COS, MDCK, Jurkat, HEK-293, and WI38.

For long-term, high-yield production of recombinant proteins, stable expression is useful. Rather than using expression vectors that contain viral origins of replication, host cells can be transformed with the cDNA encoding a fusion polypeptide of the disclosure controlled by appropriate expression control elements (e.g., promoter, enhancer, sequences, transcription terminators, polyadenylation sites, and the like), and a selectable marker. The selectable marker in the recombinant plasmid confers resistance to the selection and allows cells to stably integrate the plasmid into their chromosomes and grow to form foci that, in turn, can be cloned and expanded into cell lines. For example, following the introduction of foreign DNA, engineered cells may be allowed to grow for 1-2 days in an enriched media, and then are switched to a selective media. A number of selection systems may be used, including, but not limited to, the herpes simplex virus thymidine kinase (Wigler et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy et al., Cell, 22:817, 1980) genes can be employed in tk-, hgprt-or aprt-cells, respectively. Also, antimetabolite resistance can be used as the basis of selection for dhfr, which confers resistance to methotrexate (Wigler et al., Proc. Natl. Acad. Sci. USA, 77:3567, 1980; O'Hare et al., Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin et al., J. Mol. Biol., 150:1, 1981); and hygro, which confers resistance to hygromycin genes (Santerre et al., Gene, 30:147, 1984). Additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:8047, 1988); and ODC (ornithine decarboxylase), which confers resistance to the ornithine decarboxylase inhibitor, 2-(difluoromethyl)-DL-ornithine, DEMO (McConlogue L., In: Current Communications in Molecular Biology, Cold Spring Harbor Laboratory, ed., 1987).

Techniques for the isolation and purification of either microbially or eukaryotically expressed binding peptide-fusion polypeptides of the disclosure may be by any conventional means, such as, for example, preparative chromatographic separations and immunological separations, such as those involving the use of monoclonal or polyclonal antibodies or antigen.

Small cyclic peptides may generally be used to specifically modulate adhesion of cancer and/or other cell types by topical administration or by systemic administration, with or without linking a targeting agent to the peptide, as discussed below.

A pharmaceutical composition according to the disclosure can be prepared to include a polypeptide of the disclosure, into a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14 th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The pharmaceutical compositions according to the disclosure may be administered locally or systemically. By "therapeutically effective dose" is meant the quantity of a compound according to the disclosure necessary to prevent, to cure, or at least partially arrest the symptoms of tissue damage. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249: 1527, (1990); Gilman et al. (eds.) (1990), each of which is herein incorporated by reference.

As used herein, "administering a therapeutically effective amount" is intended to include methods of giving or applying a pharmaceutical composition of the disclosure to a subject that allow the composition to perform its intended therapeutic function. The therapeutically effective amounts will vary according to factors, such as the degree of infection in a subject, the age, sex, and weight of the individual. Dosage regima can be adjusted to provide the optimum therapeutic response. For example, several divided doses can be administered daily or the dose can be proportionally reduced as indicated by the exigencies of the therapeutic situation.

The pharmaceutical composition can be administered in a convenient manner, such as by injection (subcutaneous, intravenous, etc.), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the individual's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic in the amounts employed. In addition, the pharmaceutical composition can be incorporated into sustained-release preparations and formulations.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. "Dosage unit form" as used herein, refers to physically discrete units suited as unitary dosages for the individual to be treated; each unit containing a predetermined quantity of pharmaceutical composition is calculated to produce the desired therapeutic effect in association with the required pharmaceutical carrier. The specification for the novel dosage unit forms of the disclosure are dictated by and directly dependent on: (a) the unique characteristics of the pharmaceutical composition and the particular therapeutic effect to be achieve, and (b) the limitations inherent in the art of compounding such an pharmaceutical composition for the treatment of a pathogenic infection in a subject.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

The following examples are offered by way of illustration and not by way of limitation.

EXAMPLES

Materials. Peptides used in this study were synthesized by Abgent (San Diego, Calif.) and AnaSpec (San Jose, Calif.). Peptides were synthesized by solid-phase synthesis procedure, purified by reverse phase HPLC to >98% purity. The sequences of peptides used in the disclosure are summarized in Table 1. For immobilization to Streptavidin (SA) sensor chip (Biacore, GE), peptides were biotinylated at N-or C-terminus with GS (GGGGS) (SEQ ID NO:13) or PEG linker to increase the accessibility of peptide. Peptides were dissolved in a small amount of solvent (e.g., DMSO at 5-10% final concentration) and brought up to specific concentrations by $H_2O$; the pH was adjusted to neutral by phosphate buffer. Primers for subcloning were synthesized by IDT.

TABLE 1

Peptides and Claudin-4 Mimics Used in This Study

| Peptide | Sequence | Structure |
|---|---|---|
| Cpe30 | SLDAGQYVLVMKANSSYSGNYPYSILFQKF | Biotin(B)-PEG10-Cpe30 |
| Cpe17 | NSSYSGNYPYSILFQKF | B-PEG6-Cpe17 |
| Cpe30 MT1 | SSYSGNYPYSIL | B-PEG8-Cpe30MT1 |
| Cpe30 MT2 | NSSYSGNYYSIL | B-PEG8-Cpe30MT2 |
| Cpe30 MT3 | ASNSSYSGNYSIL | B-PEG8-Cpe30MT3 |
| CC4P-5 | SPWSEPAYTLAP | CC4P-5-PEG8-B |
| CC4P-13 | APWTEHSYYLSL | CC4P-13-PEG8-B |
| CC4GP-1 | APWHLSSQYSRT | B-PEG8-CC4GP-1 |
| CC4GP-1Y | APYHLSSQYSRT | B-PEG8-CC4GP-1Y |
| CC4P-2 | VTHKTCPPACWP | CC4P-2-PEG8-B |
| Cldn4 mimics | | |
| Ecl2 | (138)AHNVIRDFYNPMVASGQKREMGASL(160) | B-2 GS(GGGGS)-Ecl2 |
| Tethered Ecl2 | AHNVIRDFYNPMVASGQKREMGASL | B-PEG4-Ecl2-PEG4-B |
| Lariat Ecl2 | AHNVIRDFYNPMVASGQKREMGASL | B-PEG10-Cys-Ecl2-Cys |
| GST-Ecl2 | GST-Aa 138-160 | GST ----- |
| -FL | Aa 1-210 | GST 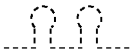 |
| -TM3 Ecl2.TM4 | Aa 117-181 | GST  |
| -TM3 Ecl2.CT | Aa 117-210 | GST  |
| -Ecl2.CT | Aa 138-210 | GST  |

Note:
Peptides were synthesized as a biotinylated form to be conjugated into streptavidin sensor chip. PGE or GS linker was added to increase the accessibility of peptide. Claudin-4 deletion mutants were expressed as a GST recombinant protein to improve the solubility of this membrane protein.

Screening Cldn4 binding peptides by phage display library. A random 12-mer peptide phage display library (Cat# E8110S, NEB, USA) was used for screening. The library size is about $2.7\times10^9$ transformants. To select phage against transmembrane Cldn4 extracellular domains, CHO cells transfected with full length Cldn4 (CHO-Cldn4) were employed for phage library selection. The screening was performed according to the manufacture's instruction with some modifications. Four rounds of panning were done, where the 1st round was selected by CHO-Cldn4 cells ("positive selection"). The 2nd round used CHO control cells ("negative selection") to remove phage specific for CHO determinants. This second, negatively selected library was followed by a $3^{rd}$ positive selection round with CHO-Cldn4 cells, and an additional $4^{th}$ negative selection round with CHO control cells. Phage clones were then isolated for sequencing of display peptide sequences, and abundant or repeated sequences were selected as candidate clones. Two positive binding peptides (CC4P-13, CC4P-5) (Table 1) were selected after 4 rounds of screening. The peptides were synthesized for SPR assay.

Protein expression and purification. Claudin-4: Mouse claudin-4 (cldn4, NM_00903) was subcloned into pGEX4T-2 by BamHI(5') and XhoI (3') by PCR high fidelity DNA polymerase Pfu (Stratagene, USA). The primers for each deletion mutant were: full length clnd4 by F1 (forward primer 1): 5'-GGATCCGCGATGGCGTCTATGGGAC-3' (SEQ ID NO:19); R1 (reverse primer 1): 5'-CTCGAGTTACACATAGTTGCTGGCGGGG-3'(SEQ ID NO:20); Ecl2 by F2: 5'-GGATCCATCATGATCACCGCCGGAG-3' (SEQ ID NO:21); R2: 5'-CTCGAGTCAGAGGAGGCCTCCTCC-3' (SEQ ID NO:22); TM3.Ecl2.CT by primer F2 and R1; and Ecl2.CT by F3: 5'-GGATCCTGGACCGCTCACAACG-3' (SEQ ID NO:23) and primer R1. The underlined sequences were BamHI and XhoI restriction sites. The constructs were confirmed by DNA sequencing. GST-Cldn4/pGEX4T-2 construct was transformed into *E. coli* (BL21, pLysS) for protein expression. The soluble protein was purified by Glutathione-agarose affinity chromatography (Pierce, USA), and the co-purified GST protein was separated by gel filtration chromatography on FPLC with Superdex 200 column. For use as the analyte in Biacore assay, GST-cldn4 was balanced to HBS-EP buffer by Microcon (Millipore) centrifugation.

Figure 6:
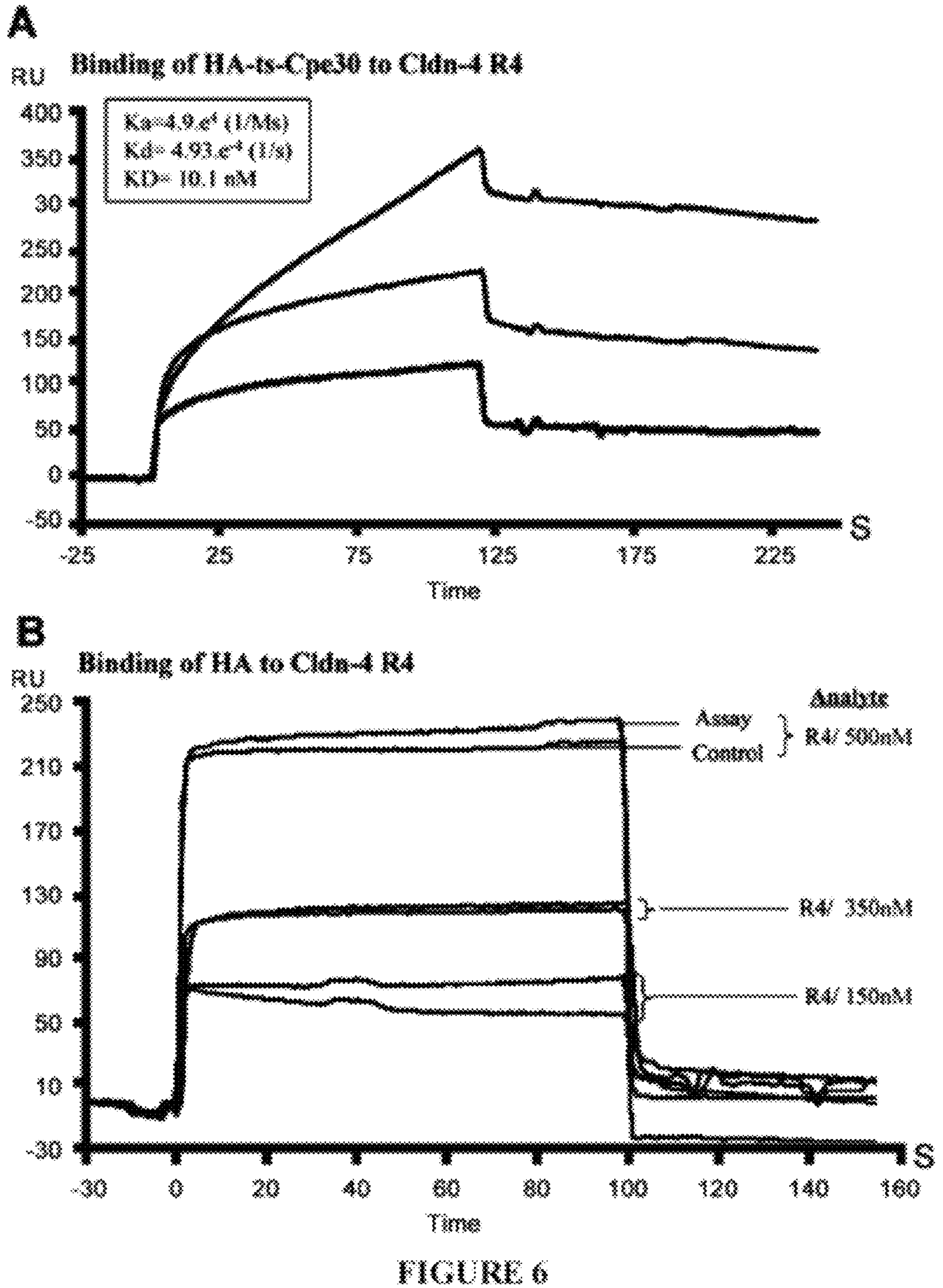

Hemagglutinin (HA): HA from influenza A virus (A/Puerto Rico/8/34/Mount Sinai, AF389118) was used to express recombinant HA protein. It was subcloned into pENTR3C vector via BamHI (5') and EcoRV (3') by PCR procedure, and recombined into BaculoDirect Linear DNA ("BaculoDirect™ Baculovirus expression system", Invitrogen, USA). The resultant expression virus was used to express protein in insect cell (Sf9). The C-terminal 37 amino acids of HA containing the transmembrane domain were removed to enable secretion of soluble protein, and a trimerization sequence (ts, from Fibritin-C) was inserted to facilitate efficient trimerization of HA. Cpe30 (the c-terminal 30 amino acids of the *Clostridium perfringens* enterotoxin) was introduced to the C-terminus with upstream GS linkers (FIG. 6). This recombinant HA (HA-cpe30) was C-terminally His tagged, and purified by HisPur Cobalt (Pierce, USA) affinity chromatography.

Measurement of binding kinetics by SPR. The BiacoreX100 system (Biacore, GE) was used in this experiment. SA (streptavidin) sensor chips were used to immobilize the biotinylated peptides. HBS-EP buffer (10 mM HEPES, 0.15M NaCl, 3 mM EDTA, 0.005% Surfactant P20, pH7.4) was used as the binding buffer. General procedures were according to manufacturer's instructions. Biotinylated peptide (e.g., Cpe30) was immobilized to the SA chip after first conditioning the chip surface with 50 mM NaOH/1M NaCl. The immobilized amount of the ligand was ~500 RU (response units) to ensure efficient binding. The control channel was treated in the same way as assay channel but without peptide immobilized. The analyte was a GST-Cldn4 protein comprised of GST fused at the C-terminal end to a fragment of Cldn4 from the second extracellular domain (Ecl2) through the C-terminus of Cldn4. The titration was measured with purified GST-Cldn4 from 0.2 uM to 2 uM in HBS-EP. GST protein only was employed as the control analyte. The binding was carried out at 25 C with flow rate at 30 ul/min, and data were collected for 2 min of association and 3 min of dissociation.

In the other assay, an HA conformation sensitive antibody (H36) was immobilized to CM5 sensor chip by amine-coupling reaction, then recombinant HA protein was indirectly captured as the ligand to interact with GST-Cldn4.R4 analyte in HBS-EP buffer as above.

To analyze the data, the assay channel was subtracted by the control channel in order to eliminate nonspecific interaction. Multiple sensorgrams from different concentrations of analyte were overlaid and aligned, and kinetic constants were calculated by BIAevaluation 3.1 software with nonlinear fitting, the 1:1 (langmuir) binding model was used, where $K_D$=kd/ka.

Measurement of peptide binding to GST-Cldn4 by co-purification. In vitro binding assays were carried out with biotinylated peptides (lug) and purified GST-Cldn4.R4 (5 ug) in HBS-EP. The binding was incubated for 1 hr at room temperature, followed by purification of the complex by immobilized Neutravidin™ affinity chromatography (Pierce, USA). The resin was washed 3 times with HBS-EP, and the bound protein was analyzed by SDS-PAGE followed by western blotting with Cldn4 antibody (Invitrogen, USA).

Claudin-4 Ecl2 in the context of transmembrane domains provides the conformation for Cpe30 binding. Claudin-4 was initially cloned as the Cpe receptor (CPE-R); consequently, Cpe, as a naturally-occurring ligand, has proven to be a useful molecular probe to study the function of Cldn-4. To measure the binding affinity, various methods were utilized. When $^{125}$I-C-Cpe comprising amino acids 184-319 of SEQ ID NO:24:

```
mlsnnlnpmv fenakevfli sedlktpini tnsnsnlsdg lyvidkgdgw ilgepsvvss
qilnpnetgt fsqsltkske vsinvnfsvg ftsefiqasv eygfgitige qntiersyst
tagpneyvyy kvyatyrkyq airishgnis ddgsiykltg iwlsktsads lgnidqgsli
etgercvltv pstdiekeil dlaaaterln ltdalnsnpa gnlydwrssn sypwtqklnl
hltltatgqk yrilaskivd fniysnnfnn lvkleqslgd gvkdhyvdis ldagqyvlvm
kanssysgny pysilfqkf
```

were used to interact with claudins over-expressed in mouse L cells, it was found that C-Cpe does not bind to Cldn-1 and Cldn-2, whereas Cldn-3 and Cldn-4 show specific binding with calculated affinity (Ka from Scatchard plot) of 8.4×10$^7$ M$^{-1}$ and 1.1×10$^8$ M$^{-1}$ respectively. In another study, a far-western approach was employed to measure the binding of purified C-Cpe to GST-Cldn3 Ecl2 protein separated by SDS-PAGE and blotted onto NC membrane; here, the Ka was calculated to be 1.0×10$^8$ M$^{-1}$. Claudin-6, 7, 8 and 14 were also tested for C-Cpe binding by this method, with affinities estimated from submicro-to micromolar levels.

Figure 1:
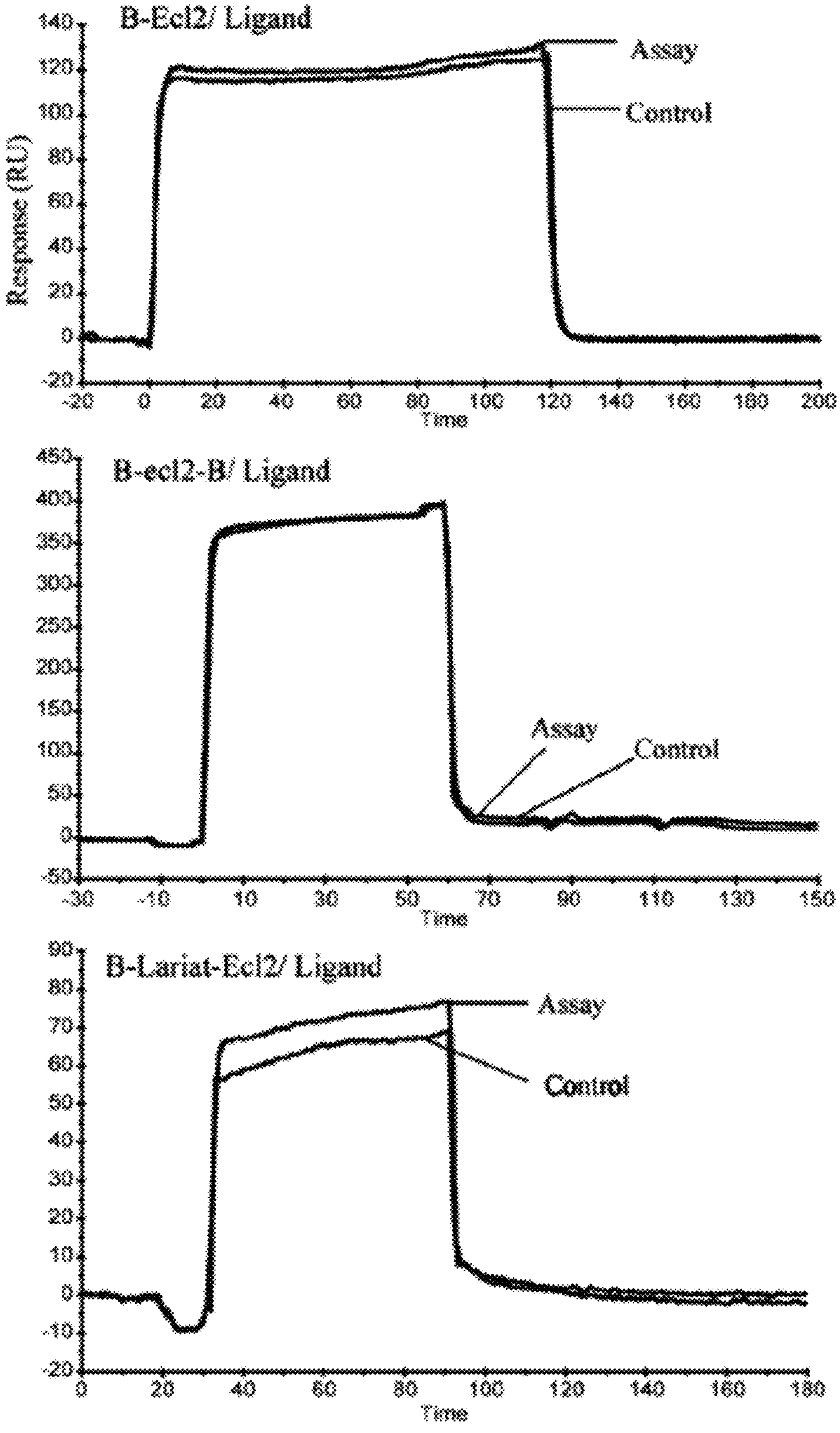
FIG. 1 shows claudin-4 Ecl2 only does not bind to Cpe30. The Claudin-4 Ecl2 domain was synthesized as a biotinylated peptide as described in Table 1. Biotin-Ecl2 peptides were immobilized to Streptavidin (SA) sensor chips at three different configurations; B-Ecl2 was a linear structure, B-Ecl2-B was tethered to streptavidin by biotins at both N-and C-termini, and B-lariat-Ecl2 contained a loop via disulfide bond formed between two cysteines flanking the Ecl2 loop. The ligands were immobilized at 500 RU, and tested against Cpe30 peptide as the analyte. The control channel was treated the same as the assay channel, but without B-peptide. The sensorgrams with 5 μM of Cpe30 are shown.

These above methods only measured the binding affinity at the end-point, and binding kinetics were not determined. Since binding on-and off-rates may be important parameters in the behavior of the peptides in vivo, a novel SPR method was developed used as described herein. The first strategy was to directly use Ecl2 peptide bound to an SA chip to interact with binding peptides. The Ecl2 sequence alone was synthesized as a biotinylated peptide (Table 1), immobilized to SA chip as the ligand, then tested against the free Cpe30 peptide as the analyte. No specific binding was observed from this assay (FIG. 1, upper panel). In an attempt to better model the conformation of the cldn-4 extracellular domain, the Ecl2 peptide was synthesized with biotin moieties at both N-and C-termini. One rationale was that such a loop would potentially be tethered to an SA chip by binding to a single tetravalent streptavidin molecule; this could present Ecl2 in a more physiological "loop" conformation. However, the result still failed to bind to Cpe30 (FIG. 1 middle panel). Another attempt at mimicking the natural Ecl2 loop was done by synthesis of Ecl2 as a cyclic peptide with a disulfide bond between two cysteines flanking the ends; this loop also failed to bind (FIG. 1 lower panel). In these attempts, the constraints on the Ecl2 loop may have failed to permit proper folding of the peptide.

The results above indicated that the isolated Cldn-4 Ecl2 alone is not sufficient for binding to Cpe30. It is likely that when Cldn-4 is in the cell membrane in vivo, the upstream and downstream transmembrane domains (TM) provide additional structural contexts to maintain Ecl2 conformation; these TMs may therefore be helpful in establishing the correct Ecl2 conformation in vitro. Thus, studies using Ecl2 in the context of other cldn-4 domains as shown in FIG. 2A was performed. The small molecular weight of Cldn-4 with 4 TMs and a strong tendency of oligomerization pose a difficult solubility problem for this protein. To enhance the solubility of these constructs, GST was fused to the N-terminus; this was helpful, though there was still significant protein in the inclusion body when expressed in BL21 (pLysS) *E. coli* strain. Soluble protein was purified by Glutathione-agarose affinity chromatography with further separation by gel-filtration. These recombinant proteins were then found to be at a purity sufficient for SPR assays (FIG. 2B).

Assays were then performed using B-Cpe30 as the ligand bound to an SA chip, and the GST-Cldn4 recombinant proteins were used as the analytes. The higher molecular weight of these analytes was also beneficial in increasing the sensitivity of the SPR assay. When these GST cldn-4 fusion proteins were tested against Cpe30, high affinity specific binding was observed. The assay channel showed a typical association and dissociation response by comparison to the control channel, which only reflected fluctuations in analyte concentration. The subtracted sensorgrams at a medium concentration of each analyte were overlaid and shown in FIG. 2C. The disclosure demonstrates that all of the Cldn-4 variants shown exhibited binding activity, suggesting that Ecl2 in the context of neighboring cldn-4 domains displayed better conformation than as a separated peptide. Sensorgrams from all fusion proteins behaved normally except for the fusion containing the full length Cldn-4. This protein showed a slight decrease in the late stages of association, raising the possibility of a two-phase interaction from interactions with Ecl1 or other parts of Cldn-4 sequence.

TM3.Ecl2.TM4 expressed a consistent binding to Cpe30, indicating that the C-terminal domain of Cldn-4 was not required for interaction with ligand, even though this domain is thought to be involved in the signaling functions of Cldn-4 in vivo. By removing the TM3 and adding the C-terminal tail (the R4 construct), the fusion protein now displayed optimal binding activity to Cpe30. Presumably, the GST moiety at the N-terminus could serve as an anchor similar to TM3. Therefore, the R4 construct was chosen as the best mimic of Ecl2 for the rest of this study. It was interesting to note that GST-Ecl2 without any TM domain also exhibited a detectable binding activity, albeit at much lower affinity. This may in part be due to GST dimerization, helping Ecl2 form a partial "loop" conformation.

Claudin-4 binding peptides exhibit different kinetics but share a common binding motif. With the establishment of this SPR method, the kinetics of binding of Cpe30 and Cpe17 to cldn-4 Ecl2 was tested. Deletion experiments have demonstrated that the last 30 amino acids of Cpe were responsible for the binding to Cldn-4. Loss of the 17 terminal amino acids also caused the loss of binding, raising the possibility that this region contained the minimal binding domain. Therefore, B-Cpe30 and Cpe17 immobilized to an SA chip as the ligand were tested, and a series of concentrations of GST-Cldn4.Ecl2 (R4) as the analyte was applied to measure binding kinetics. The results demonstrated a strong specific binding; the subtracted sensorgrams were overlaid as shown in FIG. 3. GST protein as a control did not bind Cpe30, confirming that the specific binding was from the Cldn-4 Ecl2. The 50 nM analyte concentration was repeated twice to ensure the reproducibility of the assay. The calculated equilibrium affinities ($K_D$) for Cpe30 and Cpe17 were 2.56 nM and 1.57 nM respectively, which was in the typical range of receptor-ligand binding. Kinetics analysis showed the on-rates were similar for Cpe30 and Cpe17, but Cpe17 had a slightly slower off-rate, giving it a higher calculated equilibrium affinity.

This SPR method also provided a useful tool to evaluate candidate peptides selected by phage display. To generate new short peptides with Cldn-4 binding activity, a phage display approach was used. A large library of random 12-mer display peptides allowed us to select for peptides able to bind cldn-4 under physiological conditions in vitro. Claudin-4 over-expressed in CHO cells was used as the bait for selection using alternating rounds of positive selection on transfected CHO cells, and negative selection against non-transfected cells. Starting after the third round, phage clones were sequenced, and sequences showing enrichment with successive rounds of selection were considered candidate binding clones. Peptides encoded by these sequences were then synthesized (with a peptide or PEG spacer, ending with a biotin for binding to the SA chip) and tested for specific binding to cldn-4. Three abundant peptides (CC4P-13, -5 and -2) were identified after 4 rounds of screening (Table 1). CC4P-13 was biotinylated at the C-terminus to reproduce the orientation of the peptide when displayed on the surface of the phage particle. By contrast, CC4P-13R was biotinylated at N-terminus; this orientation is similar to that in the recombinant HA fusion protein described below. The assays were performed as for Cpe30, and the sensorgrams shown in FIG. 3 demonstrated a clear specific binding of CC4P-13 and CC4P-5 peptides to Ecl2. The $K_D$ was measured at the nanomolar level, with CC4P-13R showing the slowest off-rate. CC4P-2 showed no binding to Ecl2 by this SPR assay. This could be due to several factors; this clone might be specific for CHO determinants and simply survived negative selection, it could be specific for the cldn-4 Ecl1 domain, or other unknown factors enabled its enrichment.

The SPR assay proved to be helpful in determining the specific binding and the detailed kinetics of several cldn-4-binding peptides. Interestingly, the orientation of biotinylation did not affect the binding of CC4P-13 to Ecl2, reinforcing the notion that this peptide was a true cldn-4 ligand. Such adaptable peptides could have utility in a variety of other contexts.

The disclosure shows that the binding activity of Cpe30 was abolished upon removal of the last five amino acids. Since function 12-mer peptides were identified, the possibility of a common binding motif for Cldn4 Ecl2 was analyzed. Based on the CC4P-13 and CC4P-5 similarities to Cpe30 and Cpe17, the basic Cpe30 sequence was reduced to a 12-mer. This was done by removing the last 4 amino acids and the N-terminal 13 amino acids not included in Cpe17, then the spacing between the Y306, Y310 and Y312 was modified with minimal changes in amino acid composition (Table 1). Three candidate mutant 12-mers (MT1 through MT3) were tested using the same SPR assay as in FIG. 3. MT2 was found to possess binding activity to Ecl2 with high affinity (FIG. 4), although MT1 and MT2 showed no specific binding.

Comparing the sequences among these positive binding peptides revealed an interesting pattern. As shown in FIG. 5, all of the peptides contained tyrosine or tryptophan at the position corresponding to the Y306 in Cpe, and after a 3-4 amino acids spacer there were 1 or 2 tyrosines followed by a leucine. This pattern constituted an apparent Ecl2 binding motif; it is likely that the first Y or W is the priming or docking site and the remaining Y and L residues participate in the chemical bonding of the contact.

Claudin-4 binding peptide retains binding activity in recombinant protein. Peptides with the ability to bind to cldn-4 in vivo could have many useful applications, including targeting delivery vehicles to tumors over-expressing cldn-4, or targeting vaccine antigens to mucosal M cells. For this purpose, it would be important to know whether the peptide can still function in other contexts, such as part of a recombinant fusion protein. Accordingly, tests were performed to determine whether the attachment of a targeting peptide to the c-terminal end of a recombinant influenza hemagglutinin (HA) would still retain targeting specificity.

To test this question, Cpe30 was integrated into the C-terminus of HA. The recombinant fusion protein (HA-ts-Cpe30) was produced by an insect expression system and purified for the SPR assay. The recombinant protein was captured on a CM5 chip using an anti-HA antibody (H36), which is specific for a conformational determinant on the globular head of the HA trimer. In this orientation, the HA trimer is presented with the c-terminal tail and Cpe30 domain displayed outwards for interaction with analyte. The binding to GST-Cldn4.R4 was tested as in FIG. 3. The HA fusion protein with Cpe30 exhibited strong specific binding to Ecl2, though the association seemed to be a 2-phase reaction and the on-rate was slower than free Cpe30 peptide. This is possibly due to the decreased surface accessibility caused by the c-terminal His tag. Cpe30 in HA protein could also be affected by flanking sequences to some extent, even though it was predicted to be exposed on the protein surface (Protean software (Lasergene)). When HA protein without Cpe30 was used as the ligand, no specific interaction was detectable. The addition of a cldn-4-binding peptide to a recombinant globular protein still showed binding activity even when in a heterologous context. This principle could have application in a variety of useful situations.

The active uptake of fluorescent particles was examined when coated with either a control peptide or with the cldn4 targeting peptide Cpe30. Beads were instilled into the nasal passage of BALB/c mice, and ten minutes later the NALT was removed for histological examination of bead uptake into the NALT follicle. The Cpe30-coated beads were taken up at significantly higher levels relative to control beads coated with a scrambled sequence from CC4p-13 (FIGS. 7 and 8). As another type of control, targeted uptake was examined in CD137/4-1BB knockout mice, which demonstrate defective M cell function; here the uptake of Cpe30 coated beads was only at background levels, showing the requirement for active uptake of the targeted beads. Differences between Cpe30 coated bead uptake in BALB/c and either control peptide-coated beads or CD137 knockout mice were highly significant (*$p<0.0001$).

M cell targeting of mucosal vaccines: Tissue specific titers and isotype responses. As noted above, an expression vector was developed that could incorporate the target vaccine antigen, fused with functional subunits, including spacer peptides, trimerization peptide, and M cell-targeting peptide. The first target organism was influenza. A recombinant version of the influenza hemagglutinin (HA) was produced, as neutralizing antibodies against HA would be best at blocking viral entry. A truncated form of HA lacking the transmembrane and cytoplasmic domains was produced. Such a recombinant protein forms trimers in solution, but to encourage effective trimer formation, a trimerization peptide from Fibritin-C flanked by peptide spacers was added at the C-terminal end. The M cell-targeting Cpe30 peptide, with a His tag at the end to assist in purification, was then placed at C-terminal to the trimerization peptide. The map of the expression construct is shown in FIG. 9. Then the recombinant protein was produced in baculovirus-insect cell cultures, the presence of the trimerization peptide helped stabilize HA trimers even when analyzed by non-denaturing gels (FIG. 10). Proper conformation of the protein trimers was confirmed by experiments demonstrating that the trimeric protein bound to a conformation-dependent monoclonal antibody against HA (H36). This protein proved to have cldn4-binding with similar affinity as the free Cpe30, demonstrating that the targeting peptide retained function even in the context of a fusion protein. For immunization controls, HA without the targeting Cpe30 peptide was generated.

Figure 13:
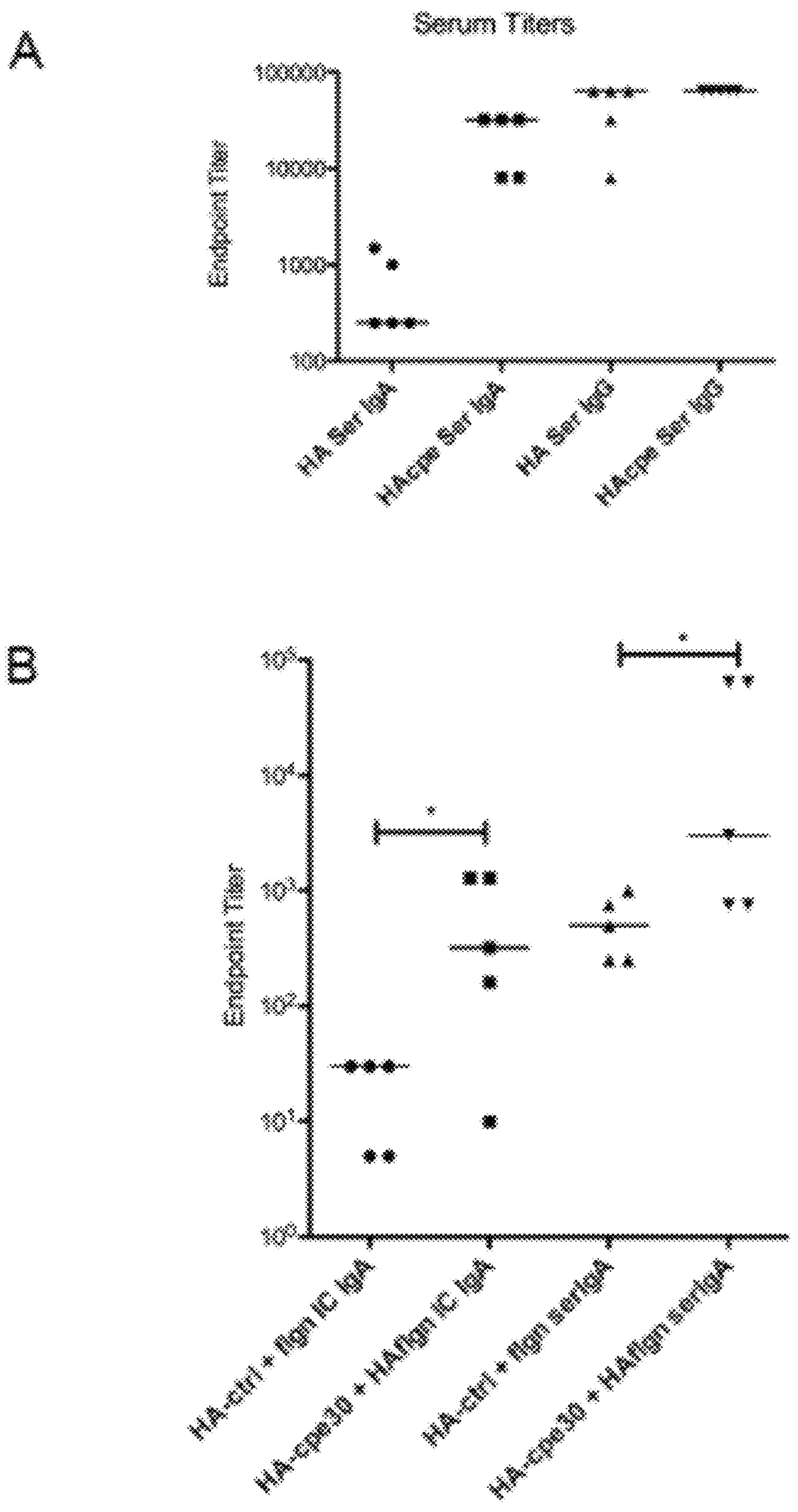

Various versions of the targeted HA vaccine were tested in mucosal immunizations of mice. BALB/c mice (5 mice per group) were immunized with three weekly intranasal doses of 2 μg HA-ts-Cpe30 or control HA with cholera toxin (1 μg) in the first dose only. On the fourth week, both groups developed similar serum IgG titers against HA, as revealed by the ELISA titration curves. In contrast to IgG titers, the targeted HA group (HA-Cpe) developed higher IgA anti-HA titers in the intestinal content (IC) than the control group (HA) (FIG. 11). In a second study, HA chemically conjugated with Cpe30 or control peptide (a scrambled peptide sequence) was used for intranasal immunization at 20 μg per dose, in combination with 5 μg flagellin per dose as an adjuvant. A higher antigen dose was required with the chemical conjugation, perhaps because the conjugation may have reduced the overall antigenicity of the recombinant HA. In this study, the targeted HA (HA-cpe) induced higher serum IgG and intestinal content IgA titers against HA than the non-targeted HA, with significantly greater intestinal IgA/IgG ratio in the targeted group than in control mice (FIG. 12). In an additional study, the purified flagellin was replaced with an HA-flagellin recombinant fusion protein, similar to the HA-ts-Cpe30-HT construct, but with the Cpe30 sequence replaced by a full length sequence of flagellin cloned from *Salmonella typhimurium*. When mixed with HA-Cpe30, this combination induced the highest intestinal and serum IgA titers of all (FIG. 13). Collectively, these three examples indicate that the targeting of the vaccine antigen to mucosal lymphoid tissues (along with a mucosal adjuvant) specifically boosts mucosal IgA responses.

Antibody responses: changing titers versus overall affinity. The immune response of immunized animals is expected to decay over time in the absence of booster immunizations or infection. The ability of a decaying antibody response to provide persistent protective immunity will depend in large part on the persistence of neutralizing titers in the most important tissues (e.g., mucosal tissues) and the affinity of the antibodies present. The affinity of Abs may have important implications on viral infection, as lower affinity Abs may enhance viral infection of myeloid cells that express Fc receptors via the ADE phenomenon.

In this context, both ELISA and the Biacore/Surface Plasmon Resonance (SPR) method were used to assess whether the method of immunization may influence not only the antibody titer, but also the affinity of the antibodies for the target antigen. SPR can be used to measure not only equilibrium affinity but also on-and off-rates of protein binding. These measurements are best performed with highly defined purified proteins, but they can also be used for qualitative studies on polyclonal antibody binding to target antigen. In studies, antibodies in serum and intestinal contents were compared from mice immunized with HA versus the M cell-targeted HA-CPE30 vaccine (FIG. 14). Precise calculations of antibody affinity are not possible for polyclonal responses, as the exact concentration of the HA-binding antibodies (relative to total Ig) cannot be measured. However, a difference in the binding of antibodies from the HA-CPE30 immunization versus HA alone or preimmune antibodies was observed. Specifically, the higher shift in resonance units induced by serum from the HA-CPE30 immunized mouse suggests a higher affinity response than seen in the mouse immunized by HA.

The disclosure demonstrates that the vaccination studies provide proof-of-principle data for the ability of an M cell-targeted vaccine to specifically induce high intestinal IgA titers against a vaccine antigen. The intranasal or oral route of immunization allows the M cell-targeted fusion protein to be potentially applicable as a needle-free vaccine that could be used in human populations. Although humans have tonsils instead of NALT, studies have confirmed that cldn4 is highly expressed in tonsil crypt epithelium, where the concentration of tonsil M cells is highest. In the context of the disclosure, this new vaccine delivery technology could be used as an effective means of inducing high intestinal IgA titers against respiratory and intestinal infectious organism antigens.

The disclosure provides a method for PLGA nanoparticle production that provides useful features for delivery to mucosal cells. First, the particles are in a narrow size range around 300 nanometers, which are an optimal size range for mucosal M cell uptake. Second, the protocol can be adapted to incorporate nearly any new protein, and the particles show a two phase release profile with a rapid phase releasing up to half of the protein over a few days, and a slow phase releasing the rest of the protein over three months. Third, the particles display most of the protein on the surface of the particles (probably accounting for the fast release phase). This presentation of the protein on the surface is quite different from particles using polymers such as PLA:PEG block co-polymers, where the protein is mainly encapsulated within the matrix. The important consequence of this distribution is that the targeting peptide on the HA-CPE protein is accessible and thus can be used for M cell targeting of the particles both in NALT and Peyer's patches. Studies in the literature suggest that PLGA might help protect the protein from digestion in the intestine.

Manufacture of vaccine HA antigen, and new HA construct with enhanced binding. The disclosure has demonstrated that CPE peptides and fragments bind to Claudin 4. Claudin 4 is a target receptor on mucosal M cells, and so a recombinant fusion proteins with the influenza hemagglutinin (HA) attached to a CPE30 peptide was developed to measure whether the fusion construct was a suitable vaccine.

Method for producing PLGA nanoparticles incorporating proteins for targeting to mucosal M cells. The objective is to develop a method for preparation of biodegradable nanoparticles loaded with recombinant proteins with targeting peptides for optimal M cell uptake.

Materials for nanoparticle preparation: PLGA poly(DL-lactide-co-glycolide (85:15 PLGA, MW 50,000-75,000) Sigma-Aldrich Catalog #430471-5G; Poly(vinyl alcohol) (PVA, MW 30,000-70,000, 87%-90% hydrolyzed) Sigma-Aldrich #P8136-250G; 4-(2-Hydroxyethyl)-1-Piperazineethanesulfonic Acid (HEPES, 1M), Invitrogen #15630-080; Phosphate Buffered Saline (PBS, 1X) Invitrogen #10010; Sodium Dodecyl Sulfate solution (10% SDS), Invitrogen #24730-020; F-12 Kaighn's medium Invitrogen #21127; geneticin Invitrogen #10131-035; Methylene Chloride optima®, Fisher #D151-1; PBS (10× ready concentrate pouches), Fisher #BP665-1; HEPES (powder fine white crystals) Fisher #BP310-500; sodium hydroxide (certified A.S.C) Fisher #S318-500; Rhodamine 6G Sigma-Aldrich #83697; 16% paraformaldehyde Electron Microscopy Services #15710; Prolong Gold antifade reagent with DAPI Molecular Probes #P36935; Pierce BCA™ Protein Assay Kit Fisher #23227 Branson® sonifier 450.

Procedure: Nanoparticle Preparation. PLGA nanoparticles containing targeting (HA-HT-CPE30) and non-targeting (HA-HT) peptides were prepared from 85:15 PLGA using solvent evaporation/double emulsion (also known as water-in oil-in water, w/o/w) method.

Preparation of stock solutions. 4% PLGA polymer solution was prepared by adding 0.18 g of PLGA into 4.5 mL of metheylene chloride in a glass beaker and stirring until dissolved. 2% PVA solution was prepared by dissolving 0.6 g of PVA in 30 ml 10 mM HEPES and adjusting the pH to 7.5 with NaOH. Protein solutions: HA-HT-CPE30 or HA-HT protein in HEPES buffer with 3.0-4.5 mg/ml concentration. For labeling experiments; a 40 mg/ml Rhodamine 6 G (R6G) solution was prepared by dissolving 1 mg of R6G in 25 μl of metheylene chloride.

Preparation of first emulsion: The reagents listed in the table were added to a 18×150 mm disposable glass tube in the order listed.

| | |
|---|---|
| 4% PLGA solution | 4.25 ml |
| Protein | 0.5 ml of HA•HT•CPE30 or HA•HT |
| 2% PVA Stabilizer | 0.25 ml |

For labeled nanoparticles, 25 μl of 40 mg/ml R6G was added to the PLGA solution before adding the protein. The solution was emulsified by probe sonication for 20 sec (Duty cycle 20%, output control 3) to obtain w/o emulsion.

The resulting w/o emulsion was divided into two 18×150 mm disposable glass tubes and 12.5 ml of 2% PVA solution was added to each tube. The solution was emulsified by probe sonication for 30 sec (Duty cycle 20%, output control 3) to obtain the final w/o/w emulsion.

The final w/o/w was then combined in a 50 ml glass beaker and stirred uncovered for 20 hours with a magnetic stirrer at 400 rpm at 4° C. to allow solvent evaporation.

The solution was added to a 40 ml Oakridge tube and centrifuged at 3800 rpm for 30 min. The supernatant was discarded and the pellet was resuspended gently in 20 ml of distilled water. The washing step was repeated with two 20 min and one 15 min centrifugation. The supernatant was discarded.

The resulting nanoparticle pellet was frozen in liquid nitrogen and lyophilized overnight at −88° C., 0.006 Torr.

The final product was stored at 4° C. and kept dry with Dry-rite calcium sulfate pellets till ready to use.

The morphology of the protein-loaded nanoparticles was visualized by Scanning Electron Microscopy (SEM). A very small amount of nanoparticles were placed on a double-sided adhesive tape attached to an aluminum stub and sputter coated with gold/palladium beam for 2 min. The coated sampled were imaged with Philips XL30-FEG SEM at 10 kV.

The particle size of the nanoparticles was measured with ImageJ software using the obtained SEM images. The diameter of approximately 150 nanoparticles was measured, and the size distribution was plotted using Prism software.

Total protein loading was estimated using BCA assay. Approximately 5-8 mg of freeze-dried nanoparticles were accurately measured and added to 2 ml of 5% SDS in 0.1 M NaOH solution and incubated with shaking for 24 hours at room temperature until a clear solution was obtained (Rafati et al., 1997). The protein content was measured in triplicates for each sample using BCA protein assay. The protein loading (%, w/w) was expressed as the amount of protein relative to the weight of the nanoparticles assayed (Coombes et al., 1998).

In vitro, the nanoparticles with the HA-HT-CPE protein were readily taken up by GFP-Claudin4 CHO transfectants, showing both the function of the targeting peptide and the accessibility of the functional targeting peptide in the nanoparticles.

In vitro uptake studies of R6G-labeled protein-loaded nanoparticles were performed in Green Fluorescence Protein (GFP) tagged claudin-4 (GFP-Cldn-4) transfected Chinese Hamster Ovary (CHO) cells (Ling et al., 2008). Cells were maintained in F-12 Kaighn's medium supplemented with 10% Fetal Bovine Serum and 0.8 mg/ml geneticin. The confocal studies were performed in 50% confluent cells plated on cover slides placed in 6-well plates, grown at 37° C. in 5% $CO_2$ incubator for 48 hrs. The cells were washed with 2 ml of PBS and the medium was replaced by 1 ml of 10 μg/ml nanoparticle solution (10 μg of protein/well), prepared by dissolving R6G-labled protein-loaded nanoparticles in culture medium pre-warmed to 37° C. The cells were incubated at 37° C. in 5% $CO_2$ incubator for one or two hrs. Upon incubation, cells were washed three times with 2 ml of PBS to remove unbound nanoparticles. Cells were then fixed with 2 ml of 4% paraformaldehyde in PBS for 20 minutes at room temperature and washed with 2 ml of PBS+0.1% Tween20 for 3-5 min for two times. The cells on the cover slides were then mounted on glass slides with Prolong Gold antifade reagent with DAPI and incubated for 24 hrs at room temperature.

Cells were analyzed using a BD CARV II spinning disc confocal microscope, using IPLab software. (see, e.g., FIG. 15).

In vivo, the same nanoparticles are also taken up in mucosal lymphoid tissues such as NALT and Peyer's patches, with a clear preference for the HA-HT-CPE targeted nanoparticles. Interestingly, the enhanced uptake is more evident for Peyer's patch, where the slower transit time of the intestinal contents may allow for the effect of the targeting peptide on M cell uptake. (See, e.g., FIG. 16).

What is claimed is:

1. A substantially purified peptide consisting of a sequence selected from the group consisting of:

```
(a) NSSYSGNYPYSILFQKF;     (SEQ ID NO: 5)

(b) SSYSGNYPYSIL;          (SEQ ID NO: 6)

(c) NSSYSGNYYSIL; and      (SEQ ID NO: 7)

(d) APWTEHSYYLSL           (SEQ ID NO: 10).
```

2. The substantially purified peptide of claim 1, wherein the peptide binds to a claudin-4 polypeptide.

3. The substantially purified peptide of claim 1 further comprising a moiety of interest linked to the peptide.

4. The substantially purified peptide of claim 3, wherein the moiety of interest is a small molecule drug, a polypeptide or peptide, an antibody, a peptidomimetic, or a nanoparticle.

5. The substantially purified peptide of claim 4, wherein the polypeptide or peptide is an immunogenic polypeptide or peptide.

6. The substantially purified peptide of claim 4, wherein the polypeptide or peptide is a therapeutic polypeptide or peptide.

7. The substantially purified peptide of claim 4, wherein the polypeptide or peptide is a growth factor.

8. The substantially purified peptide of claim 4, wherein the small molecule drug is an anticancer drug.

9. The substantially purified peptide of claim 4, wherein the nanoparticle is a metallic nanoparticle.

10. The substantially purified peptide of claim 4, wherein the nanoparticle is a biocompatible polymer.

11. The substantially purified peptide of claim 10, wherein the biocompatible polymer is poly(lactide-co-glycolide) (PLGA).

12. The substantially purified peptide of claim 11, wherein the nanoparticle comprising PLGA further comprises a therapeutic agent.

13. A substantially purified peptide consisting of a sequence selected from the group consisting of:

```
(a) NSSYSGNYPYSILFQKF;     (SEQ ID NO: 5)

(b) SSYSGNYPYSIL;          (SEQ ID NO: 6)

(c) NSSYSGNYYSIL; and      (SEQ ID NO: 7)

(d) APWTEHSYYLSL           (SEQ ID NO: 10),
```

wherein the peptide comprises at least one D-amino acid.

14. A pharmaceutical composition comprising the peptide of claim 1 or 13.

15. The composition of claim 14, in a controlled release formulation, in a liposomal form, in a lyophilized form or in a unit dosage form.

16. A fusion polypeptide comprising the peptide of claim 1 further comprising a polypeptide of interest linked to the peptide.

17. The fusion polypeptide of claim 16, wherein the polypeptide of interest comprises an immunogenic molecule.

18. The fusion peptide of claim 16, wherein the peptide and the polypeptide of interest are separated by a peptide linker.

19. A method of modulating inflammation, asthma, allergy, cell proliferative disorders, metastasis of cancer cells, ion transport disorders, magnesium transport defects in the kidney, inflammatory bowel disease, Clostridium perfringens enterotoxin (CPE) infection, myelin sheath formation disorder, multiple sclerosis (MS), autoimmune encephalomyelitis, optic neuritis, and progressive multifocal leukoencephalopathy (PML), the method comprising administering to a subject the peptide of claim 1 or 13, or a fusion polypeptide of claim 16 either alone or optionally with a pharmaceutically acceptable carrier.

20. A method of targeting a therapeutic to mucosal M cells comprising linking a therapeutic moiety to the peptide of claim 1, 13, or a fusion polypeptide of claim 16 and contacting a mucosal M cell with the peptide or fusion polypeptide.

21. The method of claim 20, wherein the mucosal M cell is in vivo.

22. The method of claim 20, wherein the therapeutic moiety is a cytotoxic drug, an immunopotentiating drug, an inhibitory nucleic acid molecule, a peptide, a polypeptide or a peptidomimetic.

* * * * *

SEQUENCE LISTING

```
<160> NUMBER OF SEQ ID NOS: 24

<210> SEQ ID NO 1
<211> LENGTH: 9
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa is Y or W
<220> FEATURE:
<221> NAME/KEY: MISC_FEATURE
<222> LOCATION: (2)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa may or may not be present, but if present
      is any amino acid
<220> FEATURE:
<221> NAME/KEY: MISC_FEATURE
<222> LOCATION: (8)..(8)
<223> OTHER INFORMATION: Xaa is any amino acid

<400> SEQUENCE: 1

Xaa Xaa Xaa Xaa Xaa Tyr Tyr Xaa Leu
1               5


<210> SEQ ID NO 2
<211> LENGTH: 13
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Y or W
<220> FEATURE:
<221> NAME/KEY: MISC_FEATURE
<222> LOCATION: (6)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa may or may not be present, but if present
      is any amino acid
<220> FEATURE:
<221> NAME/KEY: MISC_FEATURE
<222> LOCATION: (12)..(12)
<223> OTHER INFORMATION: Xaa is any amino acid

<400> SEQUENCE: 2

Xaa Xaa Xaa Xaa Xaa Xaa Xaa Xaa Xaa Tyr Tyr Xaa Leu
1               5                   10


<210> SEQ ID NO 3
<211> LENGTH: 12
<212> TYPE: PRT
<213> ORGANISM: Artificial sequence
```

-continued

<220> FEATURE:
<223> OTHER INFORMATION: Consensus sequence
<220> FEATURE:
<221> NAME/KEY: MISC_FEATURE
<222> LOCATION: (1)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is Y or W
<220> FEATURE:
<221> NAME/KEY: MISC_FEATURE
<222> LOCATION: (4)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa may or may not be present, but if present
is any amino acid
<220> FEATURE:
<221> NAME/KEY: MISC_FEATURE
<222> LOCATION: (9)..(9)
<223> OTHER INFORMATION: Xaa is Y or any amino acid
<220> FEATURE:
<221> NAME/KEY: MISC_FEATURE
<222> LOCATION: (10)..(10)
<223> OTHER INFORMATION: Xaa is L or I
<220> FEATURE:
<221> NAME/KEY: MISC_FEATURE
<222> LOCATION: (11)..(12)
<223> OTHER INFORMATION: Xaa is any amino acid

<400> SEQUENCE: 3

Xaa Xaa Xaa Xaa Xaa Xaa Xaa Tyr Xaa Xaa Xaa Xaa
1               5                   10

<210> SEQ ID NO 4
<211> LENGTH: 30
<212> TYPE: PRT
<213> ORGANISM: Artificial Sequence
<220> FEATURE:
<223> OTHER INFORMATION: Peptide fragment of CPE or derivative

<400> SEQUENCE: 4

Ser Leu Asp Ala Gly Gln Tyr Val Leu Val Met Lys Ala Asn Ser Ser
1               5                   10                  15

Tyr Ser Gly Asn Tyr Pro Tyr Ser Ile Leu Phe Gln Lys Phe
            20                  25                  30

<210> SEQ ID NO 5
<211> LENGTH: 17
<212> TYPE: PRT
<213> ORGANISM: Artificial Sequence
<220> FEATURE:
<223> OTHER INFORMATION: Peptide fragment of CPE or derivative

<400> SEQUENCE: 5

Asn Ser Ser Tyr Ser Gly Asn Tyr Pro Tyr Ser Ile Leu Phe Gln Lys
1               5                   10                  15

Phe

<210> SEQ ID NO 6
<211> LENGTH: 12
<212> TYPE: PRT
<213> ORGANISM: Artificial Sequence
<220> FEATURE:
<223> OTHER INFORMATION: Peptide fragment of CPE or derivative

<400> SEQUENCE: 6

Ser Ser Tyr Ser Gly Asn Tyr Pro Tyr Ser Ile Leu
1               5                   10

-continued

<210> SEQ ID NO 7
<211> LENGTH: 12
<212> TYPE: PRT
<213> ORGANISM: Artificial Sequence
<220> FEATURE:
<223> OTHER INFORMATION: Peptide fragment of CPE or derivative

<400> SEQUENCE: 7

Asn Ser Ser Tyr Ser Gly Asn Tyr Tyr Ser Ile Leu
1 5 10

<210> SEQ ID NO 8
<211> LENGTH: 13
<212> TYPE: PRT
<213> ORGANISM: Artificial Sequence
<220> FEATURE:
<223> OTHER INFORMATION: Peptide fragment of CPE or derivative

<400> SEQUENCE: 8

Ala Ser Asn Ser Ser Tyr Ser Gly Asn Tyr Ser Ile Leu
1 5 10

<210> SEQ ID NO 9
<211> LENGTH: 12
<212> TYPE: PRT
<213> ORGANISM: Artificial Sequence
<220> FEATURE:
<223> OTHER INFORMATION: Peptide fragment of CPE or derivative

<400> SEQUENCE: 9

Ser Pro Trp Ser Glu Pro Ala Tyr Thr Leu Ala Pro
1 5 10

<210> SEQ ID NO 10
<211> LENGTH: 12
<212> TYPE: PRT
<213> ORGANISM: Artificial Sequence
<220> FEATURE:
<223> OTHER INFORMATION: Peptide fragment of CPE or derivative

<400> SEQUENCE: 10

Ala Pro Trp Thr Glu His Ser Tyr Tyr Leu Ser Leu
1 5 10

<210> SEQ ID NO 11
<211> LENGTH: 630
<212> TYPE: DNA
<213> ORGANISM: Homo sapiens
<220> FEATURE:
<221> NAME/KEY: CDS
<222> LOCATION: (1)..(630)

<400> SEQUENCE: 11 atg gcc tcc atg ggg cta cag gta atg ggc atc gcg ctg gcc gtc ctg 48
Met Ala Ser Met Gly Leu Gln Val Met Gly Ile Ala Leu Ala Val Leu
1 5 10 15 ggc tgg ctg gcc gtc atg ctg tgc tgc gcg ctg ccc atg tgg cgc gtg 96
Gly Trp Leu Ala Val Met Leu Cys Cys Ala Leu Pro Met Trp Arg Val
20 25 30 acg gcc ttc atc ggc agc aac att gtc acc tcg cag acc atc tgg gag 144
Thr Ala Phe Ile Gly Ser Asn Ile Val Thr Ser Gln Thr Ile Trp Glu
35 40 45 ggc cta tgg atg aac tgc gtg gtg cag agc acc ggc cag atg cag tgc 192
Gly Leu Trp Met Asn Cys Val Val Gln Ser Thr Gly Gln Met Gln Cys
50 55 60

```
aag gtg tac gac tcg ctg ctg gca ctg ccg cag gac ctg cag gcg gcc      240
Lys Val Tyr Asp Ser Leu Leu Ala Leu Pro Gln Asp Leu Gln Ala Ala
65                  70                  75                  80

cgc gcc ctc gtc atc atc agc atc atc gtg gct gct ctg ggc gtg ctg      288
Arg Ala Leu Val Ile Ile Ser Ile Ile Val Ala Ala Leu Gly Val Leu
                85                  90                  95

ctg tcc gtg gtg ggg ggc aag tgt acc aac tgc ctg gag gat gaa agc      336
Leu Ser Val Val Gly Gly Lys Cys Thr Asn Cys Leu Glu Asp Glu Ser
            100                 105                 110

gcc aag gcc aag acc atg atc gtg gcg ggc gtg gtg ttc ctg ttg gcc      384
Ala Lys Ala Lys Thr Met Ile Val Ala Gly Val Val Phe Leu Leu Ala
        115                 120                 125

ggc ctt atg gtg ata gtg ccg gtg tcc tgg acg gcc cac aac atc atc      432
Gly Leu Met Val Ile Val Pro Val Ser Trp Thr Ala His Asn Ile Ile
    130                 135                 140

caa gac ttc tac aat ccg ctg gtg gcc tcc ggg cag aag cgg gag atg      480
Gln Asp Phe Tyr Asn Pro Leu Val Ala Ser Gly Gln Lys Arg Glu Met
145                 150                 155                 160

ggt gcc tcg ctc tac gtc ggc tgg gcc gcc tcc ggc ctg ctg ctc ctt      528
Gly Ala Ser Leu Tyr Val Gly Trp Ala Ala Ser Gly Leu Leu Leu Leu
                165                 170                 175

ggc ggg ggg ctg ctt tgc tgc aac tgt cca ccc cgc aca gac aag cct      576
Gly Gly Gly Leu Leu Cys Cys Asn Cys Pro Pro Arg Thr Asp Lys Pro
            180                 185                 190

tac tcc gcc aag tat tct gct gcc cgc tct gct gct gcc agc aac tac      624
Tyr Ser Ala Lys Tyr Ser Ala Ala Arg Ser Ala Ala Ala Ser Asn Tyr
        195                 200                 205

gtg taa                                                              630
Val


<210> SEQ ID NO 12
<211> LENGTH: 209
<212> TYPE: PRT
<213> ORGANISM: Homo sapiens

<400> SEQUENCE: 12

Met Ala Ser Met Gly Leu Gln Val Met Gly Ile Ala Leu Ala Val Leu
1               5                   10                  15

Gly Trp Leu Ala Val Met Leu Cys Cys Ala Leu Pro Met Trp Arg Val
            20                  25                  30

Thr Ala Phe Ile Gly Ser Asn Ile Val Thr Ser Gln Thr Ile Trp Glu
        35                  40                  45

Gly Leu Trp Met Asn Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Val Ile Ile Ser Ile Ile Val Ala Ala Leu Gly Val Leu
                85                  90                  95

Leu Ser Val Val Gly Gly Lys Cys Thr Asn Cys Leu Glu Asp Glu Ser
            100                 105                 110

Ala Lys Ala Lys Thr Met Ile Val Ala Gly Val Val Phe Leu Leu Ala
        115                 120                 125

Gly Leu Met Val Ile Val Pro Val Ser Trp Thr Ala His Asn Ile Ile
    130                 135                 140

Gln Asp Phe Tyr Asn Pro Leu Val Ala Ser Gly Gln Lys Arg Glu Met
145                 150                 155                 160

Gly Ala Ser Leu Tyr Val Gly Trp Ala Ala Ser Gly Leu Leu Leu Leu
                165                 170                 175
```

-continued

```
Gly Gly Gly Leu Leu Cys Cys Asn Cys Pro Pro Arg Thr Asp Lys Pro
            180                 185                 190

Tyr Ser Ala Lys Tyr Ser Ala Ala Arg Ser Ala Ala Ala Ser Asn Tyr
        195                 200                 205

Val


<210> SEQ ID NO 13
<211> LENGTH: 5
<212> TYPE: PRT
<213> ORGANISM: Artificial Sequence
<220> FEATURE:
<223> OTHER INFORMATION: Peptide linker

<400> SEQUENCE: 13

Gly Gly Gly Gly Ser
1               5


<210> SEQ ID NO 14
<211> LENGTH: 12
<212> TYPE: PRT
<213> ORGANISM: Artificial Sequence
<220> FEATURE:
<223> OTHER INFORMATION: Peptide Linker

<400> SEQUENCE: 14

Gly Lys Ser Ser Gly Ser Gly Ser Glu Ser Lys Ser
1               5                   10


<210> SEQ ID NO 15
<211> LENGTH: 14
<212> TYPE: PRT
<213> ORGANISM: Artificial Sequence
<220> FEATURE:
<223> OTHER INFORMATION: Peptide Linker

<400> SEQUENCE: 15

Gly Ser Thr Ser Gly Ser Gly Lys Ser Ser Glu Gly Lys Gly
1               5                   10


<210> SEQ ID NO 16
<211> LENGTH: 18
<212> TYPE: PRT
<213> ORGANISM: Artificial Sequence
<220> FEATURE:
<223> OTHER INFORMATION: Peptide Linker

<400> SEQUENCE: 16

Gly Ser Thr Ser Gly Ser Gly Lys Ser Ser Glu Gly Ser Gly Ser Thr
1               5                   10                  15

Lys Gly


<210> SEQ ID NO 17
<211> LENGTH: 18
<212> TYPE: PRT
<213> ORGANISM: Artificial Sequence
<220> FEATURE:
<223> OTHER INFORMATION: Peptide Linker

<400> SEQUENCE: 17

Gly Ser Thr Ser Gly Ser Gly Lys Pro Gly Ser Gly Glu Gly Ser Thr
1               5                   10                  15

Lys Gly


<210> SEQ ID NO 18
<211> LENGTH: 14
```

<212> TYPE: PRT
<213> ORGANISM: Artificial Sequence
<220> FEATURE:
<223> OTHER INFORMATION: Peptide Linker

<400> SEQUENCE: 18

Glu Gly Lys Ser Ser Gly Ser Gly Ser Glu Ser Lys Glu Phe
1 5 10

<210> SEQ ID NO 19
<211> LENGTH: 25
<212> TYPE: DNA
<213> ORGANISM: Artificial Sequence
<220> FEATURE:
<223> OTHER INFORMATION: Forward Primer

<400> SEQUENCE: 19
ggatccgcga tggcgtctat gggac 25

<210> SEQ ID NO 20
<211> LENGTH: 28
<212> TYPE: DNA
<213> ORGANISM: Artificial Sequence
<220> FEATURE:
<223> OTHER INFORMATION: Reverse Primer

<400> SEQUENCE: 20
ctcgagttac acatagttgc tggcgggg 28

<210> SEQ ID NO 21
<211> LENGTH: 25
<212> TYPE: DNA
<213> ORGANISM: Artificial Sequence
<220> FEATURE:
<223> OTHER INFORMATION: Forward Primer

<400> SEQUENCE: 21
ggatccatca tgatcaccgc cggag 25

<210> SEQ ID NO 22
<211> LENGTH: 24
<212> TYPE: DNA
<213> ORGANISM: Artificial Sequence
<220> FEATURE:
<223> OTHER INFORMATION: Reverse Primer

<400> SEQUENCE: 22
ctcgagtcag aggaggcctc ctcc 24

<210> SEQ ID NO 23
<211> LENGTH: 22
<212> TYPE: DNA
<213> ORGANISM: Artificial Sequence
<220> FEATURE:
<223> OTHER INFORMATION: Forward Primer

<400> SEQUENCE: 23
ggatcctgga ccgctcacaa cg 22

<210> SEQ ID NO 24
<211> LENGTH: 319
<212> TYPE: PRT
<213> ORGANISM: Homo sapiens

<400> SEQUENCE: 24

Met Leu Ser Asn Asn Leu Asn Pro Met Val Phe Glu Asn Ala Lys Glu
1 5 10 15

-continued

```
Val Phe Leu Ile Ser Glu Asp Leu Lys Thr Pro Ile Asn Ile Thr Asn
            20                  25                  30

Ser Asn Ser Asn Leu Ser Asp Gly Leu Tyr Val Ile Asp Lys Gly Asp
        35                  40                  45

Gly Trp Ile Leu Gly Glu Pro Ser Val Val Ser Ser Gln Ile Leu Asn
    50                  55                  60

Pro Asn Glu Thr Gly Thr Phe Ser Gln Ser Leu Thr Lys Ser Lys Glu
65                  70                  75                  80

Val Ser Ile Asn Val Asn Phe Ser Val Gly Phe Thr Ser Glu Phe Ile
                85                  90                  95

Gln Ala Ser Val Glu Tyr Gly Phe Gly Ile Thr Ile Gly Glu Gln Asn
            100                 105                 110

Thr Ile Glu Arg Ser Val Ser Thr Thr Ala Gly Pro Asn Glu Tyr Val
        115                 120                 125

Tyr Tyr Lys Val Tyr Ala Thr Tyr Arg Lys Tyr Gln Ala Ile Arg Ile
    130                 135                 140

Ser His Gly Asn Ile Ser Asp Asp Gly Ser Ile Tyr Lys Leu Thr Gly
145                 150                 155                 160

Ile Trp Leu Ser Lys Thr Ser Ala Asp Ser Leu Gly Asn Ile Asp Gln
                165                 170                 175

Gly Ser Leu Ile Glu Thr Gly Glu Arg Cys Val Leu Thr Val Pro Ser
            180                 185                 190

Thr Asp Ile Glu Lys Glu Ile Leu Asp Leu Ala Ala Ala Thr Glu Arg
        195                 200                 205

Leu Asn Leu Thr Asp Ala Leu Asn Ser Asn Pro Ala Gly Asn Leu Tyr
    210                 215                 220

Asp Trp Arg Ser Ser Asn Ser Tyr Pro Trp Thr Gln Lys Leu Asn Leu
225                 230                 235                 240

His Leu Thr Ile Thr Ala Thr Gly Gln Lys Tyr Arg Ile Leu Ala Ser
                245                 250                 255

Lys Ile Val Asp Phe Asn Ile Tyr Ser Asn Asn Phe Asn Asn Leu Val
            260                 265                 270

Lys Leu Glu Gln Ser Leu Gly Asp Gly Val Lys Asp His Tyr Val Asp
        275                 280                 285

Ile Ser Leu Asp Ala Gly Gln Tyr Val Leu Val Met Lys Ala Asn Ser
    290                 295                 300

Ser Tyr Ser Gly Asn Tyr Pro Tyr Ser Ile Leu Phe Gln Lys Phe
305                 310                 315
```